United States Patent [19]
Dellaporta

[11] Patent Number: 6,013,486
[45] Date of Patent: Jan. 11, 2000

[54] METHOD FOR SELECTION OF INSERTION MUTANTS

[75] Inventor: Stephen L. Dellaporta, Branford, Conn.

[73] Assignee: Yale University, New Haven, Conn.

[21] Appl. No.: 08/932,280

[22] Filed: Sep. 17, 1997

[51] Int. Cl.[7] .............................. C12P 19/34; C12Q 1/68; C07H 21/02; C07H 21/04
[52] U.S. Cl. .......................... 435/91.2; 435/6; 435/91.1; 435/172.1; 536/23.1; 536/24.31; 536/24.32
[58] Field of Search .............................. 435/6, 91.2, 91.1, 435/410, 441, 172.1

[56] References Cited

U.S. PATENT DOCUMENTS

| | | | |
|---|---|---|---|
| 4,683,202 | 7/1987 | Mullis | 435/91 |
| 4,994,370 | 2/1991 | Silver et al. | 435/6 |
| 5,576,197 | 11/1996 | Arnold et al. | 435/91.2 |
| 5,807,522 | 9/1998 | Brown et al. | 422/50 |

FOREIGN PATENT DOCUMENTS

| | | |
|---|---|---|
| WO 95/00530 | 1/1995 | WIPO . |
| WO 96/39803 | 12/1996 | WIPO . |

OTHER PUBLICATIONS

Arnold and Hodgson, "Vectorette PCR: A Novel Approach to Genomic Walking," *PCR Methods and Applications*, 1:39–42, 1991.

Ballinger and Benzer, "Targeted Gene Mutations in Drosophila," *Proc. Natl. Acad. Sci. USA*, 86:9402–9406, Dec. 1989.

Beattie et al., "Advances in Genosensor Research," *Clin. Chem.*, 41(5):700–706, 1995.

Beattie et al., "Hybridization of DNA Targets to Glass–Tethered Oligonucleotide Probes," *Molecular Biotechnology*, 4:1–8, 1995.

Bensen et al., "Cloning and Characterization of the maize An1 Gene," *The Plant Cell*, 7:75–84, Jan. 1995.

Eggers et al., A Microchip for Quantitative Detection of Molecules Utilizing Luminescent and Radioisotope Reporter Groups, *Biotechniques*, 17(3):516–524, 1994.

Espelund and Jakobsen, "Cloning and Direct Sequencing of Plant Promoters Using Primer–Adapter Mediated PCR on DNA Coupled to a Magnetic Solid Phase," *Biotechniques*, 13(1):74–81, 1992.

Kaiser and Goodwin, ""Site–Selected" Transposon Mutagenesis of Drosophila," *Proc. Natl. Acad. Sci. USA*, 87:1686–1690, Mar. 1990.

Koes et al., "Targeted Gene Inactivation in Petunia by PCR–Based Selection of Transposon Insertion Mutants," *Proc. Natl. Acad. Sci. USA*, 92:8149–8153, Aug. 1995.

Krysan et al., "Identification of Transferred DNA Insertions within Arabidopsis Genes Involved in Signal Transduction and Ion Transport," *Proc. Natl. Acad. Sci. USA*, 93:8145–8150, Jul. 1996.

Lamture et al., "Direct Detection of Nucleic Acid Hybridization on the Surface of a Charge Coupled Device," *Nucleic Acids Research*, 22(11):2121–2125, 1994.

McKinney et al., "Sequence–Based Identification of T–DNA Insertion Mutations in Arabidopsis: Actin Mutants act2–1 and act4–1," *The Plant Journal*, 8(4):613–622, 1995.

Ochman, Gerber, and Hartl, "Genetic Applications of an Inverse Polymerase Chain Reaction," *Genetics*, 120:621–623, Nov. 1988.

O'Hare, "Searching for Needles in Haystacks Via the Polymerase Chain Reaction," *TIG*, 6(7):202–203, Jul. 1990.

Piétu et al., "Novel Gene Transcripts Preferentially Expressed in Human Muscles Revealed by Quantitative Hybridization of a High Density cDNA Array," *Genome Research*, 6:492–503, 1996.

Riley et al., "A Novel, Rapid method for the Isolation of Terminal Sequences from yeast Artificial Chromosome (YAC) Clones," *Nucleic Acids Research*, 18(10):2887–2890, 1990.

Rushforth, Saari, and Anderson, "Site–Selected insertion of the Transposon Tc1 into a *Caenorhabditis elegans* Myosin Light Chain Gene," *Molecular and Cellular Biology*, 13(2):902–910, Feb. 1993.

Souer et al., "A General Method to Isolate Genes Tagged by a High Copy Number Transposable Element," *The Plant Journal*, 7(4):677–685, 1995.

Southern, "DNA Chips: Analysing Sequence by hybridization to Oligonucleotides on a Large Scale," *TIG*, 12(3):110–115, Mar. 1996.

"Storage Conditions: 4° C. for Human Genomic DNA–20° C. all other Components," Universal Genome Walker™ Kit User Manual, Clontech Laboratories, Inc., Palo Alto, CA 94303–4230, USA. 1996.

Zwaal et al., "Target–Selected Gene Inactivation in *Caenorhabditis elegans* by Using a Frozen Transposon Insertion Mutant Bank," *Proc. Natl. Acad. Sci. USA*, 90:7431–7435, Aug. 1993.

Eggert et al Genetics. 149(3) abstract, 1 page, 1998.
Sentry J.W. et al NAR vol. 22, No. 16 pp. 3429–3430, 1994.
Das et al The Plant Cell vol. 7, pp. 287–294, 1995.

*Primary Examiner*—Kenneth R. Horlick
*Assistant Examiner*—Jeffrey Siew
*Attorney, Agent, or Firm*—Arnold, White & Durkee

[57] ABSTRACT

The present invention provides a highly-efficient method for the selection and identification of insertional mutants. In the technique, a non-selective amplification is used to isolate a plurality of insertion events from a population of individuals comprising insertion mutations. Specific insertion events can then be identified from the population by the use of gene specific probes or primers. Through the identification of mutants for a particular gene, data may be obtained regarding the function and phenotypic effects of that gene, and thereby, the gene can be employed in the creation of novel biotechnological products.

23 Claims, No Drawings

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 6743 base pairs
       (B) TYPE: nucleic acid
       (C) STRANDEDNESS: single
       (D) TOPOLOGY: linear (xi) SEQUENCE DESCRIPTION: SEQ ID NO:1:

```
AGTACTTTGA TCCAACCCCT CCGCTGCTAT AGTGCAGTCG GCTTCTGACG TTCAGTGCAG     60

CCGTCTTCTG AAAACGACAT GTCGCACAAG TCCTAAGTTA CGCGACAGGC TGCCGCCCTG    120

CCCTTTTCCT GGCGTTTTCT TGTCGCGTGT TTTAGTCGCA TAAAGTAGAA TACTTGCGAC    180

TAGAACCGGA GACATTACGC CATGAACAAG AGCGCCGCCG CTGGCCTGCT GGGCTATGCC    240

CGCGTCAGCA CCGACGACCA GGACTTGACC AACCAACGGG CCGAACTGCA CGCGGCCGGC    300

TGCACCAAGC TGTTTTCCGA GAAGATCACC GGCACCAGGC GCGACCGCCC GGAGCTGGCC    360

AGGATGCTTG ACCACCTACG CCCTGGCGAC GTTGTGACAG TGACCAGGCT AGACCGCCTG    420

GCCCGCAGCA CCCGCGACCT ACTGGACATT GCCGAGCGCA TCCAGGAGGC CGGCGCGGGC    480

CTGCGTAGCC TGGCAGAGCC GTGGGCCGAC ACCACCACGC CGGCCGGCCG CATGGTGTTG    540

ACCGTGTTCG CCGGCATTGC CGAGTTCGAG CGTTCCCTAA TCATCGACCG CACCCGGAGC    600

GGGCGCGAGG CCGCCAAGGC CCGAGGCGTG AAGTTTGGCC CCCGCCCTAC CCTCACCCCG    660

GCACAGATCG CGCACGCCCG CGAGCTGATC GACCAGGAAG GCCGCACCGT GAAAGAGGCG    720

GCTGCACTGC TTGGCGTGCA TCGCTCGACC CTGTACCGCG CACTTGAGCG CAGCGAGGAA    780

GTGACGCCCA CCGAGGCCAG GCGGCGCGGT GCCTTCCGTG AGGACGCATT GACCGAGGCC    840

GACGCCCTGG CGGCCGCCGA GAATGAACGC CAAGAGGAAC AAGCATGAAA CCGCACCAGG    900

ACGGCCAGGA CGAACCGTTT TTCATTACCG AAGAGATCGA GGCGGAGATG ATCGCGGCCG    960

GGTACGTGTT CGAGCCGCCC GCGCACGTCT CAACCGTGCG GCTGCATGAA ATCCTGGCCG   1020

GTTTGTCTGA TGCCAAGCTG GCGGCCTGGC CGGCCAGCTT GGCCGCTGAA GAAACCGAGC   1080

GCCGCCGTCT AAAAAGGTGA TGTGTATTTG AGTAAAACAG CTTGCGTCAT GCGGTCGCTG   1140

CGTATATGAT GCGATGAGTA AATAAACAAA TACGCAAGGG GAACGCATGA AGGTTATCGC   1200

TGTACTTAAC CAGAAAGGCG GGTCAGGCAA GACGACCATC GCAACCCATC TAGCCCGCGC   1260

CCTGCAACTC GCCGGGGCCG ATGTTCTGTT AGTCGATTCC GATCCCCAGG GCAGTGCCCG   1320

CGATTGGGCG GCCGTGCGGG AAGATCAACC GCTAACCGTT GTCGGCATCG ACCGCCCGAC   1380

GATTGACCGC GACGTGAAGG CCATCGGCCG GCGCGACTTC GTAGTGATCG ACGGAGCGCC   1440

CCAGGCGGCG GACTTGGCTG TGTCCGCGAT CAAGGCAGCC GACTTCGTGC TGATTCCGGT   1500

GCAGCCAAGC CCTTACGACA TATGGGCCAC CGCCGACCTG GTGGAGCTGG TTAAGCAGCG   1560

CATTGAGGTC ACGGATGGAA GGCTACAAGC GGCCTTTGTC GTGTCGCGGG CGATCAAAGG   1620

CACGCGCATC GGCGGTGAGG TTGCCGAGGC GCTGGCCGGG TACGAGCTGC CCATTCTTGA   1680

GTCCCGTATC ACGCAGCGCG TGAGCTACCC AGGCACTGCC GCCGCCGGCA CAACCGTTCT   1740

TGAATCAGAA CCCGAGGGCG ACGCTGCCCG CGAGGTCCAG GCGCTGGCCG CTGAAATTAA   1800

ATCAAAACTC ATTTGAGTTA ATGAGGTAAA GAGAAAATGA GCAAAAGCAC AAACACGCTA   1860
```

```
AGTGCCGGCC GTCCGAGCGC ACGCAGCAGC AAGGCTGCAA CGTTGGCCAG CCTGGCAGAC     1920

ACGCCAGCCA TGAAGCGGGT CAACTTTCAG TTGCCGGCGG AGGATCACAC CAAGCTGAAG     1980

ATGTACGCGG TACGCCAAGG CAAGACCATT ACCGAGCTGC TATCTGAATA CATCGCGCAG     2040

CTACCAGAGT AAATGAGCAA ATGAATAAAT GAGTAGATGA ATTTTAGCGG CTAAAGGAGG     2100

CGGCATGGAA AATCAAGAAC AACCAGGCAC CGACGCCGTG GAATGCCCCA TGTGTGGAGG     2160

AACGGGCGGT TGGCCAGGCG TAAGCGGCTG GGTTGTCTGC CGGCCCTGCA ATGGCACTGG     2220

AACCCCCAAG CCCGAGGAAT CGGCGTGACG GTCGCAAACC ATCCGGCCCG GTACAAATCG     2280

GCGCGGCGCT GGGTGATGAC CTGGTGGAGA AGTTGAAGGC CGCGCAGGCC GCCCAGCGGC     2340

AACGCATCGA GGCAGAAGCA CGCCCCGGTG AATCGTGGCA AGCGGCCGCT GATCGAATCC     2400

GCAAAGAATC CCGGCAACCG CCGGCAGCCG GTGCGCCGTC GATTAGGAAG CCGCCCAAGG     2460

GCGACGAGCA ACCAGATTTT TTCGTTCCGA TGCTCTATGA CGTGGGCACC CGCGATAGTC     2520

GCAGCATCAT GGACGTGGCC GTTTTCCGTC TGTCGAAGCG TGACCGACGA GCTGGCGAGG     2580

TGATCCGCTA CGAGCTTCCA GACGGGCACG TAGAGGTTTC CGCAGGGCCG GCCGGCATGG     2640

CCAGTGTGTG GGATTACGAC CTGGTACTGA TGGCGGTTTC CCATCTAACC GAATCCATGA     2700

ACCGATACCG GGAAGGGAAG GGAGACAAGC CCGGCCGCGT GTTCCGTCCA CACGTTGCGG     2760

ACGTACTCAA GTTCTGCCGG CGAGCCGATG GCGGAAAGCA GAAAGACGAC CTGGTAGAAA     2820

CCTGCATTCG GTTAAACACC ACGCACGTTG CCATGCAGCG TACGAAGAAG GCCAAGAACG     2880

GCCGCCTGGT GACGGTATCC GAGGGTGAAG CCTTGATTAG CCGCTACAAG ATCGTAAAGA     2940

GCGAAACCGG GCGGCCGGAG TACATCGAGA TCGAGCTAGC TGATTGGATG TACCGCGAGA     3000

TCACAGAAGG CAAGAACCCG GACGTGCTGA CGGTTCACCC CGATTACTTT TTGATCGATC     3060

CCGGCATCGG CCGTTTTCTC TACCGCCTGG CACGCCGCGC CGCAGGCAAG GCAGAAGCCA     3120

GATGGTTGTT CAAGACGATC TACGAACGCA GTGGCAGCGC CGGAGAGTTC AAGAAGTTCT     3180

GTTTCACCGT GCGCAAGCTG ATCGGGTCAA ATGACCTGCC GGAGTACGAT TTGAAGGAGG     3240

AGGCGGGGCA GGCTGGCCCG ATCCTAGTCA TGCGCTACCG CAACCTGATC GAGGGCGAAG     3300

CATCCGCCGG TTCCTAATGT ACGGAGCAGA TGCTAGGGCA AATTGCCCTA GCAGGGGAAA     3360

AAGGTCGAAA AGGTCTCTTT CCTGTGGATA GCACGTACAT TGGGAACCCA AAGCCGTACA     3420

TTGGGAACCG GAACCCGTAC ATTGGGAACC CAAAGCCGTA CATTGGGAAC CGGTCACACA     3480

TGTAAGTGAC TGATATAAAA GAGAAAAAAG GCGATTTTTC CGCCTAAAAC TCTTTAAAAC     3540

TTATTAAAAC TCTTAAAACC CGCCTGGCCT GTGCATAACT GTCTGGCCAG CGCACAGCCG     3600

AAGAGCTGCA AAAAGCGCCT ACCCTTCGGT CGCTGCGCTC CCTACGCCCC GCCGCTTCGC     3660

GTCGGCCTAT CGCGGCCGCT GGCCGCTCAA AAATGGCTGG CCTACGGCCA GGCAATCTAC     3720

CAGGGCGCGG ACAAGCCGCG CCGTCGCCAC TCGACCGCCG GCGCCCACAT CAAGGCACCC     3780

TGCCTCGCGC GTTTCGGTGA TGACGGTGAA AACCTCTGAC ACATGCAGCT CCCGGAGACG     3840

GTCACAGCTT GTCTGTAAGC GGATGCCGGG AGCAGACAAG CCCGTCAGGG CGCGTCAGCG     3900

GGTGTTGGCG GGTGTCGGGG CGCAGCCATG ACCCAGTCAC GTAGCGATAG CGGAGTGTAT     3960

ACTGGCTTAA CTATGCGGCA TCAGAGCAGA TTGTACTGAG AGTGCACCAT ATGCGGTGTG     4020

AAATACCGCA CAGATGCGTA AGGAGAAAAT ACCGCATCAG GCGCTCTTCC GCTTCCTCGC     4080

TCACTGACTC GCTGCGCTCG GTCGTTCGGC TGCGGCGAGC GGTATCAGCT CACTCAAAGG     4140

CGGTAATACG GTTATCCACA GAATCAGGGG ATAACGCAGG AAAGAACATG TGAGCAAAAG     4200

GCCAGCAAAA GGCCAGGAAC CGTAAAAAGG CCGCGTTGCT GGCGTTTTTC CATAGGCTCC     4260
```

-continued

```
GCCCCCCTGA CGAGCATCAC AAAAATCGAC GCTCAAGTCA GAGGTGGCGA AACCCGACAG    4320

GACTATAAAG ATACCAGGCG TTTCCCCCTG GAAGCTCCCT CGTGCGCTCT CCTGTTCCGA    4380

CCCTGCCGCT TACCGGATAC CTGTCCGCCT TTCTCCCTTC GGGAAGCGTG GCGCTTTCTC    4440

ATAGCTCACG CTGTAGGTAT CTCAGTTCGG TGTAGGTCGT TCGCTCCAAG CTGGGCTGTG    4500

TGCACGAACC CCCCGTTCAG CCCGACCGCT GCGCCTTATC CGGTAACTAT CGTCTTGAGT    4560

CCAACCCGGT AAGACACGAC TTATCGCCAC TGGCAGCAGC CACTGGTAAC AGGATTAGCA    4620

GAGCGAGGTA TGTAGGCGGT GCTACAGAGT TCTTGAAGTG GTGGCCTAAC TACGGCTACA    4680

CTAGAAGGAC AGTATTTGGT ATCTGCGCTC TGCTGAAGCC AGTTACCTTC GGAAAAAGAG    4740

TTGGTAGCTC TTGATCCGGC AAACAAACCA CCGCTGGTAG CGGTGGTTTT TTTGTTTGCA    4800

AGCAGCAGAT TACGCGCAGA AAAAAAGGAT CTCAAGAAGA TCCTTTGATC TTTTCTACGG    4860

GGTCTGACGC TCAGTGGAAC GAAAACTCAC GTTAAGGGAT TTTGGTCATG CATGATATAT    4920

CTCCCAATTT GTGTAGGGCT TATTATGCAC GCTTAAAAAT AATAAAAGCA GACTTGACCT    4980

GATAGTTTGG CTGTGAGCAA TTATGTGCTT AGTGCATCTA ATCGCTTGAG TTAACGCCGG    5040

CGAAGCGGCG TCGGCTTGAA CGAATTTCTA GCTAGACATT ATTTGCCGAC TACCTTGGTG    5100

ATCTCGCCTT TCACGTAGTG GACAAATTCT TCCAACTGAT CTGCGCGCGA GGCCAAGCGA    5160

TCTTCTTCTT GTCCAAGATA AGCCTGTCTA GCTTCAAGTA TGACGGGCTG ATACTGGGCC    5220

GGCAGGCGCT CCATTGCCCA GTCGGCAGCG ACATCCTTCG GCGCGATTTT GCCGGTTACT    5280

GCGCTGTACC AAATGCGGGA CAACGTAAGC ACTACATTTC GCTCATCGCC AGCCCAGTCG    5340

GGCGGCGAGT TCCATAGCGT TAAGGTTTCA TTTAGCGCCT CAAATAGATC CTGTTCAGGA    5400

ACCGGATCAA AGAGTTCCTC CGCCGCTGGA CCTACCAAGG CAACGCTATG TTCTCTTGCT    5460

TTTGTCAGCA AGATAGCCAG ATCAATGTCG ATCGTGGCTG GCTCGAAGAT ACCTGCAAGA    5520

ATGTCATTGC GCTGCCATTC TCCAAATTGC AGTTCGCGCT TAGCTGGATA ACGCCACGGA    5580

ATGATGTCGT CGTGCACAAC AATGGTGACT TCTACAGCGC GGAGAATCTC GCTCTCTCCA    5640

GGGGAAGCCG AAGTTTCCAA AAGGTCGTTG ATCAAAGCTC GCCGCGTTGT TTCATCAAGC    5700

CTTACGGTCA CCGTAACCAG CAAATCAATA TCACTGTGTG GCTTCAGGCC GCCATCCACT    5760

GCGGAGCCGT ACAAATGTAC GGCCAGCAAC GTCGGTTCGA GATGGCGCTC GATGACGCCA    5820

ACTACCTCTG ATAGTTGAGT CGATACTTCG GCGATCACCG CTTCCCCCAT GATGTTTAAC    5880

TTTGTTTTAG GGCGACTGCC CTGCTGCGTA ACATCGTTGC TGCTCCATAA CATCAAACAT    5940

CGACCCACGG CGTAACGCGC TTGCTGCTTG GATGCCCGAG GCATAGACTG TACCCCAAAA    6000

AAACATGTCA TAACAAGAAG CCATGAAAAC CGCCACTGCG CCGTTACCAC CGCTGCGTTC    6060

GGTCAAGGTT CTGGACCAGT TGCGTGACGG CAGTTACGCT ACTTGCATTA CAGCTTACGA    6120

ACCGAACGAG GCTTATGTCC ACTGGGTTCG TGCCCGAATT GATCACAGGC AGCAACGCTC    6180

TGTCATCGTT ACAATCAACA TGCTACCCTC CGCGAGATCA TCCGTGTTTC AAACCCGGCA    6240

GCTTAGTTGC CGTTCTTCCG AATAGCATCG GTAACATGAG CAAAGTCTGC CGCCTTACAA    6300

CGGCTCTCCC GCTGACGCCG TCCCGGACTG ATGGGCTGCC TGTATCGAGT GGTGATTTTG    6360

TGCCGAGCTG CCGGTCGGGG AGCTGTTGGC TGGCTGGTGG CAGGATATAT TGTGGTGTAA    6420

ACAAATTGAC GCTTAGACAA CTTAATAACA CATTGCGGAC GTTTTTAATG TACTGAATTA    6480

ACGCCGAATT GAATTCGAGC TCGGTACCCG GGGATCCTCT AGAGTCGACC TGCAGGCATG    6540

CAAGCTTAGC TTGAGCTTGG ATCAGATTGT CGTTTCCCGC CTTCAGTTTA AACTATCAGT    6600

GTTTGACAGG ATATATTGGC GGGTAAACCT AAGAGAAAAG AGCGTTTATT AGAATAACGG    6660
```

```
-continued

ATATTTAAAA GGGCGTGAAA AGGTTTATCC GTTCGTCCAT TTGTATGTGC ATGCCAACCA    6720

CAGGGTTCCC CTCGGGATCA AAC                                           6743
```

METHOD FOR SELECTION OF INSERTION MUTANTS

BACKGROUND OF THE INVENTION

1. Field of the Invention

The present invention relates generally to the field of molecular biology. More particularly, it concerns methods and compositions for the identification and selection of insertional mutants.

2. Description of Related Art

Mutants are powerful tools in the investigation of physiological, developmental, and cell biological processes. Starting with a phenotypic mutant generated by chemical mutagenesis, it is possible to use a genetic map-based strategy to clone a gene (Arondel et al., 1992). Mutations derived from insertional mutagenesis are particularly useful in that they provide "tagged" copies of the mutated gene which may readily be cloned (Yanofsky et al., 1990). However, molecular genetic techniques have advanced such that today most genes are cloned and sequenced long before their function is characterized genetically (Newman et al., 1994). For many genes, phenotypic screens are not available, and mutations which cause lethality remain undetectable. What has been missing is a simple and reliable strategy to go from a gene or protein sequence to the identification of specific mutants.

One solution to problems associated with mutant identification was to use the polymerase chain reaction (PCR) to screen for P-element mutations in sequenced genes of Drosophila (Ballinger et al., 1989; Kaiser et al., 1990). This approach also enhanced the genetics of Caenorhabditis (Rushforth et al., 1993; Zwaal et al., 1993), where transposable element mutations are now commonly isolated for known gene sequences. In these systems, transposon-induced mutations are isolated for known gene sequences by the general strategy known as "site-selected" mutagenesis. Basically, the method relies on the power of PCR to amplify a collection of specific junction fragments between an inserted element and a known target gene sequence from large pools of randomly inserted elements. One primer is used which is homologous to the end of the inserted element with its 3' end facing outward and one primer within the target gene is used to amplify the sequences at the junction of the insertion. In plants, similar approaches have been used to identify insertion mutations in Petunia, using the transposon dTph1 (Koes et al. 1995), and in Arabidopsis using collections of T-DNA transformed lines (Krysan et al., 1996; Mckinney et al., 1995). In Krysan et al. (1996), 9100 independent T-DNA-transformed Arabidopsis lines (averaging 1.4 insertions per genome) were subjected to site-selected mutagenesis and 17 T-DNA insertions within 63 genes were identified.

While techniques based on the gene-specific amplification of insertional junctions have been useful in the isolation of a number of mutants, they have had limited success in applications toward large-scale genomic investigations. The need for individual amplifications of each gene being investigated represents a significant hindrance when seeking to identify more than a small number of insertional mutants. There is, therefore, a great need in the art for a method by which large numbers of insertional mutants may be rapidly and efficiently identified.

SUMMARY OF THE INVENTION

The present invention seeks to overcome deficiencies in the prior art by providing a highly efficient method for selecting insertion events. Therefore, one apsect of the current invention is a method for identifying an insertion event in a genome comprising the steps of: (a) preparing a first DNA composition enhanced for a plurality of insertion junctions; (b) preparing at least a first detectable array including the first DNA composition; and (c) detecting the insertion event from the first array. The step of preparing a first DNA composition may comprise amplification of insertion junctions with inverse PCR, vectorette PCR, primer-adapted PCR, AIMS or any other suitable procedure. The method can further comprise preparing at least a second DNA composition, and additionally any greater number of DNA compositions desired by the user of the invention. The additional DNA compositions may be prepared on the same, or other arrays, as desired by the user of the invention.

In another aspect of the invention, the detectable array can comprise the first and second DNA compositions arranged on a solid support. The solid support can be a microscope slide, and the insertion event can be detected by hybridization with a fluorescently labeled probe comprising cloned DNA, and/or be detected by hybridization with a probe labeled with an antigen, where the antigen is detected with a molecule which binds the antigen. Alternatively, the insertion event can be detected by PCR. In another embodiment of the invention, the array has a solid support comprising a nitrocellulose filter, and the insertion event can be detected by hybridization with a radioactively-labeled probe comprising cloned DNA. The method of detecting can further comprise hybridization of a gene-specific probe to the array. In particular embodiments, the DNA compositions of the array will comprise DNA which has been pooled from multiple individuals. The DNA in the compositions can be derived from potentially any species, including DNA from plants, animals, prokaryotes and lower eukaryotes. In particular embodiments, the DNA may be from a monocot plant, and may further defined as from maize, rice, wheat, barley, sorghum, oat, or sugarcane. In other embodiments, the monocot DNA is maize DNA. The plant DNA may also be dicot DNA, and may be derived from a species selected from the group consisting of cotton, tobacco, tomato, soybean, sunflower, oil seed rape (canola), alfalfa, potato, strawberry, onion, broccoli, Arabidopsis, pepper, and citrus. In particular embodiments of the invention the dicot plant DNA is *Arabidopsis thaliana* DNA. In still other embodiments the DNA is animal DNA.

Still yet another aspect of the invention provides a method of determining the function of a DNA sequence. In particular embodiments of the invention the method comprises the steps of: (a) amplifying a plurality of insertion junctions from a DNA composition comprising insertion mutations; (b) creating at least a first array comprising said insertion junctions; (c) detecting at least a first mutation in said DNA sequence from said array using a primer or probe specific to said DNA sequence; and (d) determining the function of said DNA sequence by comparing individuals comprising said mutation in said DNA sequence to corresponding individuals lacking said mutation in said DNA sequence. In the method, the DNA composition may comprise plant DNA. In particular embodiments the plant DNA may be further defined as monocot plant DNA, and may be still further defined as derived from a species selected from the group consisting of maize, rice, wheat, barley, sorghum, oat, and sugarcane. In particular embodiments, the monocot DNA comprises maize DNA. The plant DNA can also comprise dicot plant DNA, and may be still further defined as derived from a species selected from the group consisting of cotton, tobacco, tomato, soybean, sunflower, oil seed rape (canola), alfalfa, potato, strawberry, onion, broccoli, Arabidopsis, pepper, and citrus. In particular embodiments, the DNA composition is *Arabidopsis thaliana* DNA.

Still yet another aspect of the invention provides a method for isolating a plant comprising a desired integration event. In particular embodiments of the invention, the method comprises the steps of: (a) integratively transforming a plurality of plants; (b) obtaining DNA from said plants; (c) amplifying a plurality of transgene insertion junctions from said DNA; (d) preparing at least a first array comprising said amplified insertion junctions; and (e) detecting a desired integration event with a probe or primer corresponding a preselected genomic region. In particular embodiments, the plant may be further defined as a monocot plant, and may be still further defined as derived from a species selected from the group consisting of maize, rice, wheat, barley, sorghum, oat, and sugarcane. In other embodiments, the monocot plant is a maize plant. The plant can also comprise a dicot plant, and may be still further defined as a species selected from the group consisting of cotton, tobacco, tomato, soybean, sunflower, oil seed rape (canola), alfalfa, potato, strawberry, onion, broccoli, Arabidopsis, pepper, and citrus. In particular embodiments, the plant is an *Arabidopsis thaliana* plant.

Still yet another aspect of the invention provides a plant preparable by a process comprising the steps of: (a) integratively transforming a plurality of plants; (b) obtaining DNA from said plants; (c) amplifying a plurality of transgene insertion junctions from said DNA; (d) preparing at least a first array comprising said amplification insertion junctions; and (e) detecting a plant having a desired transgene insertion event using a probe or primer corresponding to the selected genomic region. The plant may be further defined as a monocot plant, wherein the monocot plant may be still further defined as a monocot plant selected from the group consisting of maize, rice, wheat, barley, sorghum, oat, and sugarcane. In particular embodiments the monocot plant is maize. The plant may also be a dicot plant, and in particular embodiments, still further defined as selected from the group consisting of cotton, tobacco, tomato, soybean, sunflower, oil seed rape (canola), alfalfa, potato, strawberry, onion, broccoli, Arabidopsis, pepper, and citrus. In particular embodiments the dicot plant is an *Arabidopsis thaliana* plant.

DESCRIPTION OF ILLUSTRATIVE EMBODIMENTS

The present invention represents a significant advance over prior methods for identifying insertional mutations in that it allows for the simultaneous screening of large numbers of unique insertion events. Therefore, the first step of the invention, in one embodiment, will involve obtaining or generating a population of individuals with insertional mutations from which to screen for the mutant of interest. A preferred population will represent a large number of insertional mutations such that there will be a high probability of identifying a mutant for any given locus within the population. In a preferred embodiment, the next step will generally involve isolating DNA from the population of insertional mutations and creating pools which contain DNA from various different combinations of individuals. The pools are designed such that, through analysis of multiple pools, sequences representing single members of a population can be identified without the need for individual analysis of each member of the population. The insertion junctions present in each pool are then amplified non-selectively, providing a broad class of "tagged" insertion junctions which can subsequently be detected by use of gene-specific probes or primers. An efficient means employed for the detection of amplified insertion junctions in the pools is the preparation of arrays arranged on a suitable solid support material. The labeled gene-specific probes may then be hybridized and detected directly on the arrays, allowing simultaneous screening of a large number of pools and ultimate identification of one or more insertional mutants.

The probability of successfully identifying a chosen insertional mutant with the current invention will be greatly influenced by the characteristics of the starting population(s) from which insertional mutants will be screened. One important characteristic of the population will be the number of insertional mutations it contains. It will, of course, be preferred that any such population contain a sufficient number of insertion events that there is a reasonable likelihood of detecting at least one insertional mutant from any particular gene or locus. As such, the mechanism by which insertional mutations are generated will be important to the degree of ease with which the current invention may be used. While insertion mutations caused by potentially any known sequence long enough to be amplified may be detected with the current invention, certain types of insertions will offer advantages. Preferred insertion mutations will be predominately or completely randomly distributed throughout the target genome. This will decrease the likelihood that a particular locus is lacking an insertion mutation in the generated population and also reduce the size of the population needed to have a reasonable probability of detecting any given insertion mutation. Also preferred will be insertional mutagens which are capable of producing large numbers of mutations both within individuals and within populations, thereby increasing the effective number of mutations which may be obtained and subsequently screened. The insertion mutations created will also preferably alter gene expression for the mutated gene copy, allowing studies to elucidate the mutated genes' phenotypic effect and function, and potentially creating valuable new phenotypes.

Examples of types of insertion mutations which are contemplated to be of particular utility with the current invention will be those created by transposable elements and transgenes introduced by transformation. Which type of these, or another, insertion mutations is utilized with the current invention will typically depend on factors including the organism being studied, available resources, and the goal of the study. For example, in many dicot plants, transformation with the T-DNA of Agrobacterium may be readily achieved and large numbers of transformants can be rapidly obtained. In some monocot plants, however, transformation is less efficient and requires tissue culture steps which are comparatively time- and labor-intensive, making transformation a much less attractive alternative. Also, some species have lines with active transposable elements which can efficiently be used for the generation of large numbers of insertion mutations, while some other species lack such options. In particular instances, it may be advantageous to screen multiple types of insertion mutations, thereby increasing the chance of detecting any given desired mutant. Therefore, a number of factors will be taken into account when choosing the type(s) of insertion mutation to be identified with the current invention. These factors will be readily apparent to those of skill in the art in light of the present disclosure and will dependent on the specific goals of the investigation.

(i) Target Organism for Use with the Invention

The current invention is applicable to any species for which insertional mutants may be obtained. As such, it is specifically contemplated by the inventor that one may wish to use the current invention for the identification of specific insertion events from plants, animals, lower eukaryotes and prokaryotes. Examples of some animals for which the current invention may be used include poultry, dairy and beef cattle, primates, rodents, swine and insects. Examples of plants which are specifically contemplated for use with the current invention include monocots such as maize, rice, wheat, barley, sorghum, oat, and sugarcane, as well as dicots such as cotton, tobacco, tomato, soybean, sunflower, oil seed rape (canola), alfalfa, potato, strawberry, onion, broccoli, Arabidopsis, pepper, and citrus. Maize and Arabidopsis represent target plant species which will be particularly advantageous for use with the current invention.

(ii) Utilization of Transposon-Generated Insertion Mutations

Transposable-elements are an extremely versatile class of insertional mutagen in that a great variety of transposable elements have been identified, with representative elements having been found in all eukaryotic genomes examined (Flavell et al., 1992). As used herein, the term "transposable element" will mean any mobile genetic element which is capable of replicative or non-replicative transposition within a genome, causing insertional mutagenesis at the site of insertion. One example of a transposable element of maize contemplated to have particular utility in the generation of insertion mutations is the Mutator element (Bennetzen, 1984; Talbert et al., 1989; see Genbank Accession Numbers: x14224, x14225, g22495, g22466, g22373, m76978 and x97569). Other examples of transposable elements which are deemed particularly useful insertional mutagens are the Ac element (Geiser et al., 1982; U.S. Pat. No. 4,732,856, specifically incorporated herein by reference in its entirety) and the tobacco element slide-124 (Grappin et al, 1996; Genbank Accession Number x97569).

(iii) Generation of Insertionally Mutagenized Plant Cells by Transformation

There are many methods for transforming DNA segments into cells, but not all are suitable for delivering DNA to plant cells. Suitable methods are believed to include virtually any method by which DNA can be introduced into a cell, such as by Agrobacterium infection (described in, for example, U.S. Pat. No. 5,591,616, specifically incorporated herein by reference in its entirety); direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253), by agitation with silicon carbide fibers (Kaeppler et al. 1990), and by acceleration of DNA coated particles (U.S. Pat. No. 5,550,318), etc. Through the application of techniques such as these, certain cells from virtually any plant species may be stably transformed, and these cells developed into transgenic plants. In certain embodiments, acceleration methods are preferred and include, for example, microprojectile bombardment and the like.

One type of insertional mutations which will be of particular use in the current invention are those caused by the T-DNA of Agrobacterium. An important advantage of T-DNA-based insertions is that they are apparently randomly distributed in any given genome (reviewed by Tinland, 1996). This has been confirmed in Arabidopsis, where a uniform distribution at the chromosomal level and a random distribution within translated and untranslated regions of genes was shown (Aspiroz-Leehan and Feldman, 1997). Moreover, sequence analysis of target sites shows that: (i) integration is not site-specific; (ii) T-DNA integration can lead to small deletions (13–72 bp) at the site of insertion; and (iii) the left-end border of integrated T-DNA is usually poorly conserved as compared to the right border sequences, which can be conserved up to the nucleotide that is covalently attached to the VirD2 movement protein (Tinland, 1996). Additionally, one or more T-DNA loci (chromosomal integration sites) can frequently be found integrated into the genome of a plant cell, and the same cell can carry T-DNAs derived from different Agrobacteria cells (DeBlock et al., 1991; Depicker, 1995). Frequently, the structure of the T-DNA at a locus can be complex, involving the integration of direct and inverted T-DNA repeats.

1. Electroporation

Where one wishes to introduce DNA by means of electroporation, it is contemplated that the method of Krzyzek et al. (U.S. Pat. No. 5,384,253, incorporated herein by reference in its entirety) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding.

To effect transformation by electroporation, one may employ either friable tissues, such as a suspension culture of cells or embryogenic callus, or alternatively one may transform immature embryos or other organized tissue directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol, dependent on the nature of the newly incorporated DNA.

2. Microprojectile Bombardment

A further advantageous method for delivering transforming DNA segments to plant cells is microprojectile bombardment (U.S. Pat. No. 5,550,318; U.S. Pat. No. 5,538,880; U.S. Pat. No. 5,610,042; and PCT Patent Publication No. 94/09699; each specifically incorporated herein by reference in its entirety). In this method, particles may be coated with nucleic acids and delivered into cells by a propelling force. Exemplary particles include those comprised of tungsten, gold, platinum, and the like. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An advantage of microprojectile bombardment, in addition to its being an effective means of reproducibly stably transforming monocots, is that neither the isolation of protoplasts (Christou et al., 1988) nor the susceptibility to Agrobacterium infection is required. An illustrative embodiment of a method for delivering DNA into maize cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Examples of species for which the Biolistics Particle Delivery System has been successfully used for transformation include monocot species such as maize, barley, wheat, rice, and sorghum, as well as various dicot species, including tobacco, soybean, cotton, sunflower, and tomato.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. If desired, one or more screens may be positioned between the acceleration device and the cells to be bombarded.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in the manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various bombardment parameters in small scale studies to fully optimize the conditions. One may particularly wish to adjust physical parameters, such as gap distance, flight distance, tissue distance, helium pressure, and microprojectile particle size. One may also minimize the trauma reduction factors (TRFs) by modifying conditions which influence the physiological state of the recipient cells and which may therefore influence transformation and integration efficiencies. For example, the osmotic state, tissue hydration, and the subculture stage or cell cycle of the recipient cells may be adjusted for optimum transformation. Results from such small scale optimization studies are disclosed herein, and the execution of other routine adjustments will be known to those of skill in the art in light of the present disclosure (see, for example, PCT Patent Publication No. 94/09699, specifically incorporated herein by reference in its entirety).

3. Agrobacterium-Mediated Transfer

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art (Fraley et al., 1983; Rogers et al., 1987). Further, the integration of the T-DNA is a relatively precise process resulting in few rearrangements. The region of DNA to be transferred is defined by the border sequences, and the intervening DNA is usually inserted into the plant genome as described (Spielmann et al., 1986; Jorgensen et al., 1987).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer. An example of one T-DNA which will be especially useful with the current invention will be that of SEQ. ID NO. 1.

Agrobacterium-mediated transformation of leaf disks and other tissues, such as cotyledons and hypocotyls, appears to be limited to plants that Agrobacterium naturally infects. Agrobacterium-mediated transformation is most efficient in dicotyledonous plants and is the preferable method for transformation of dicots, including Arabidopsis, tobacco, tomato, and potato. Few monocots appear to be natural hosts for Agrobacterium, although transgenic plants have been produced in asparagus using Agrobacterium vectors as described (Bytebier et al., 1987). Therefore, commercially important cereal grains, such as rice, corn, and wheat must usually be transformed using alternative methods. Agrobacterium-mediated transformation of maize and rice has, however, been described in U.S. Pat. No. 5,591,616, specifically incorporated herein by reference in its entirety.

One efficient means by which Agrobacterium plant transformation can be mediated is by way of vacuum infiltration. This procedure is based on the vacuum infiltration of a suspension of Agrobacterium cells containing a binary T-DNA vector into plant tissue, such as, for example, from Arabidopsis plants. Exemplary procedures for vacuum infiltration are known to those of skill in the art and are disclosed in Bechtold and Bouchez (1995); and Bechtold et al. (1993), each of which is specifically incorporated herein by reference in its entirety.

A transgenic plant formed using Agrobacterium transformation methods typically contains a single transgene or a few copies of a transgene on one chromosome. Such transgenic plants can be referred to as being hemizygous. For detection of an insertional mutagen, such a plant may be preferred, in that many of the mutations may be recessive lethals. Where the mutation is not a recessive lethal, a preferred plant may be homozygous for the added structural gene, i.e., a transgenic plant that contains two added genes, one gene at the same locus on each chromosome of a chromosome pair. A homozygous transgenic plant can be obtained by sexually mating (selfing) a hemizygous transgenic plant that contains a single added gene, germinating some of the seed produced, and analyzing the resulting plants.

It is to be understood that two different transgenic plants can also be mated to produced offspring that contain multiple, independently-segregating added, insertion events. Specifically contemplated by the inventor, is the creation of plants which contain 1, 2, 3, 4, 5, or even more independently-segregating added insertion events. Selfing of appropriate progeny can produce plants that are homozygous for all added insertion mutations. Back-crossing to a parental plant and out-crossing with a non-transgenic plant are also contemplated.

4. Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; From et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimara et al., 1985; Toriyama et al., 1986; Yamada et al., 1986; Abdullah et al., 1986; Omirulleh et al., and 1993 U.S. Pat. No. 5,508,184; each specifically incorporated herein by reference in its entirety).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, pollen-mediated transformation may be used (U.S. Pat. No. 5,629,183; specifically incorporated herein by reference) In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

(iv) Generation of Insertionally Mutagenized Animal Cells by Transformation

In certain embodiments of the invention, animal cells comprising novel insertional mutants may be created by integrative transformation of recipient animal cells. Through such methods, which are well known to those of skill in the art, and others set forth herein, insertional mutants may be created for virtually any animal, plant, prokaryote or lower eukaryote. Specific methods contemplated by the inventor to be of use in the creation of insertional mutants are disclosed herein.

An example of a method of DNA delivery to recipient cells which may be used is viral infection, where a particular construct is encapsulated in an infectious viral particle. For use herein, the virus will be one which directs integrative transformation of the transformed cell. Non-viral methods for the transfer of foreign DNA into recipient cells also are contemplated in the present invention. In one embodiment of the present invention, the construct may consist only of naked DNA or plasmids; however, almost any DNA segment which is capable of insertionally mutating a target locus and which has a known sequence may potentially be used with the current invention. Transfer of the DNA may be performed by any of the methods mentioned which physically or chemically permeabilize the cell membrane.

1. Liposome-Mediated Transfection

Foreign DNA may be delivered to cells by way of liposomes. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991). It is contemplated that one may wish to complex the DNA to be delivered with Lipofectamine (Gibco BRL).

Liposome-mediated nucleic acid delivery of foreign DNA in vitro has been demonstrated to be a reliable means of transformation (Nicolau et al., 1982; Fraley et al., 1979; Nicolau et al., 1987). Wong et al. (1980) demonstrated the feasibility of liposome-mediated delivery and expression of foreign DNA in cultured chick embryo, HeLa, and hepatoma cells.

In certain embodiments, the liposomes may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with both HVJ and HMG-1.

2. Electroporation

In certain embodiments of the present invention, insertionally mutagenized animal cells may be created via electroporation. Electroporation involves the exposure of a suspension of cells and DNA to a high-voltage electric discharge. This technique is widely applicable to virtually any eukaryotic cell and may also be used for transformation of prokaryotes.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

3. Calcium Phosphate Precipitation or DEAE-Dextran Treatment

In other embodiments of the present invention, the foreign DNA may be introduced to the cells using calcium phosphate precipitation. Human KB cells have been transfected with adenovirus DNA (Graham et al., 1973) using this technique. Also in this manner, mouse L(A9), mouse C127, CHO, CV-1, BHK, NIH3T3, and HeLa cells were transfected with a neomycin marker gene (Chen and Okayama, 1987), and rat hepatocytes were transfected with a variety of marker genes (Rippe et al., 1990).

In another embodiment, the foreign DNA may be delivered into the cell using DEAE-dextran followed by polyethylene glycol. In this manner, reporter plasmids were introduced into mouse myeloma and erythroleulemia cells (Gopal, 1985).

4. Direct Microinjection or Sonication Loading

In still further embodiments of the invention, insertionally mutagenized animal cells may be created by the delivery of foreign DNA with microinjection or sonication loading. Direct microinjection has been used to introduce nucleic acid constructs into Xenopus oocytes (Harland and Weintraub, 1985), and LTK⁻ fibroblasts have been transfected with the thymidine kinase gene by sonication loading (Fechheimer et al., 1987). A similar method involves injecting a polyamino acid/DNA complex into the cytoplasm of animal cells to effect transformation (U.S. Pat. No. 5,523,222 specifically incorporated herein by reference).

5. Receptor-Mediated Transfection

A still further method for delivery of foreign DNA involves the delivery of constructs to the target cells with receptor-mediated delivery vehicles. These take advantage of the selective uptake of macromolecules by receptor-mediated endocytosis that will be occurring in the target cells. In view of the cell type-specific distribution of various receptors, this delivery method adds another degree of specificity to the transformation. Specific delivery in the context of another mammalian cell type is described by Wu and Wu (1993).

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Perales et al., 1994; European Patent No. 0 273 085), which establishes the operability of the technique. In the context of the present invention, the ligand will be chosen to correspond to a receptor specifically expressed on the neuroendocrine target cell population.

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al. (1987) employed lactosyl-ceramide, a galactose-terminal asialganglioside, incorporated into liposomes and observed an increase in the uptake of the insulin gene by hepatocytes.

Therefore, transformation of host species may be used in a similar manner to transposon-tagging. In transposon tagging, as with integrative transformation, insertion mutations are created in the genomes of target organisms by transposable elements. This creates mutant individuals from which mutant phenotypes can be identified. DNA can then be isolated from the mutants and used for the creation of genomic libraries. The mutated gene can then be efficiently cloned through the use the transposon as a "tag". Typically, a number of candidate genes will first be identified. These may then be confirmed by complementation experiments or DNA sequencing and homology searches for related known genes.

I. Amplification of Insertion Junctions

An important aspect of the current invention is that it allows selection of specific insertional mutants from a diverse class of insertion events. For this purpose, one step of the invention utilizes the non-selective amplification of insertion junctions. As used herein, the term "non-selective amplification" is used to denote amplification procedures which will simultaneously amplify a broad class of insertion junctions without the need for a single gene-specific primer. Techniques which are contemplated by the inventor as being particularly useful for the non-specific amplification are inverse PCR, vectorette PCR, and primer-adapted PCR, with vectorette PCR being most preferred, although potentially any method capable of amplifying a diverse class of insertion junctions may be used.

(i) Inverse PCR

Inverse polymerase chain reaction (IPCR) is an extension of the polymerase chain reaction that permits the amplification of regions that flank any DNA segment of known sequence, either upstream or downstream (see U.S. Pat. No. 4,994,370, specifically incorporated herein by reference in its entirety). The essence of IPCR is that, by circularizing a restriction enzyme fragment containing a region of known sequence plus flanking DNA, PCR can be performed using oligonucleotides whose sequence is taken from the single region of known sequence and oriented with respect to one another such that their 5' to 3' extension products proceed toward each other by going "around the circle" through what originally was flanking DNA. This leads to the amplification of DNA strands containing what was originally flanking DNA. The advantage of a technique such as IPCR, with respect to the current invention, is that using a single primer set one may amplify a representative sample of insertion junctions from a particular group of individuals.

Selection of appropriate restriction enzymes for use in IPCR can be determined empirically by Southern blotting and hybridization procedures using all or part of the core region. Selection of the appropriate fragment can be facilitated by computer search methods, since in most cases the entire nucleotide sequence of the core (e.g., well characterized insertional mutagens such as transposable elements or transgenes) region will be known. The amplified fragment should be no greater than 2–3 kilobases (kb), which is a limitation imposed by the size of a region that can be efficiently amplified using the most commonly available methods of PCR. However, recently PCR techniques have been developed, termed Long PCR, which are capable of amplifying DNA fragments of 20 kb or more.

After restriction enzyme digestion, the DNA fragments produced by the restriction enzyme are diluted and ligated under conditions that favor the formation of monomeric circles (Collins et al., 1984). The resulting intramolecular ligation products are then used as substrates for enzymatic amplification by PCR using oligonucleotide primers homologous to the ends of the core sequence but facing in opposite orientations. The primary product of the resulting amplification is a linear double-stranded molecule including segments situated both 5' and 3' to the core region. The junction between the original upstream and downstream regions, otherwise ambiguous, can be identified as the restriction site of the restriction enzyme that was used to produce the linear fragments prior to ligation. By selecting a restriction enzyme that cleaves inside a known core sequence, the IPCR procedure will produce products containing only the upstream or only the downstream flanking regions.

(ii) Vectorette PCR

There are three basic steps in the technique of vectorette PCR: (1) digestion of target DNA with one or more suitable restriction enzymes; (2) ligation of suitable synthetic oligonucleotides onto the digested DNA; and (3) PCR using a specific primer and a primer directed toward the synthetic oligonucleotides (see European Patent No. 0 439 330, specifically incorporated herein by reference in its entirety). In this procedure, nonspecific amplification of all digested fragments is avoided by the design of specific fragments of synthetic DNA, called vectorettes. Vectorettes are designed so that they can be amplified only if they are attached to the DNA insertional mutagen. The vectorette is only partially double-stranded and contains a central mismatched region. The vectorette PCR primer has the same sequence as the bottom strand of this mismatched region and therefore has no complementary sequence to anneal to in the first cycle of PCR. In the first cycle of PCR, only the known primer, which is directed toward the insertional mutagen, will prime DNA synthesis. This will produce a complementary strand for the vectorette PCR primer to anneal to in the second cycle of PCR. In the second and subsequent cycles of PCR, both primers can prime synthesis, with the end result being that the only fragment amplified contains the insertional mutagen and flanking DNA of the insertion site.

(iii) Primer Adapted PCR

The primer-adapted PCR technique is a derivation of ligation-mediated single-sided PCR (Fors et al., 1990; Mueller et al., 1989). This method uses linker ligation and subsequent amplifications with a linker-primer and multiple insertional-mutagen-specific primers ("nested" primers) to obtain specificity. The ligation-mediated single-sided PCR protocol involves multiple PCRs and subsequent purifications on agarose gels.

The amplification procedure involves, as a first step, restriction with an appropriate restriction enzyme, such as Sau3AI, and ligation of primer adapters to the different DNA size fractions. Then, approximately 50 cycles of linear amplification are performed using an internal biotinylated primer complimentary to the insertional mutagen. The biotinylated linear PCR product is purified from the rest of the genomic DNA with streptavidin-coated magnetic beads and subjected to exponential PCR using the adapter-primer and the insertional-mutagen specific primer. The result of this first round of exponential PCR may be visualized on an agarose gel and used in the preparation of arrays. Successful, specific amplification should be indicated by a series of bands on the agarose gel.

In order to avoid the purification steps required because of non-specificity in the PCR, an additional step may be introduced that involves linear amplification of the target sequence with a biotinylated primer and separation of the product with the aid of streptavidin-coated magnetic beads (Hultman et al., 1989; Rosenthal and Jones, 1990). This strategy may be employed in combination with ligation of oligo-cassettes to restricted DNA to directly amplify unknown regions which flank an insertional mutagen (Rosenthal and Jones, 1990).

The basic concept of the method is to employ an "internal" primer complementary to a known sequence in the insertional mutagen in combination with an "external" adapter-primer. First, primer adapters are ligated onto the genomic DNA digested with a suitable enzyme (for example, Sau3AI), then a linear PCR is performed with the insertional mutagen-complimentary primer, which is biotinylated. Since the linear PCR product is biotinylated, it can then be purified from the rest of the genomic DNA with the aid of streptavidin-coated magnetic beads. After the magnetic purification, an exponential PCR is carried out using the internal primer in combination with the adapter-primer. An extra round of PCR with a nested internal primer and the adapter-primer can be performed to achieve increased specificity. The amplified product can then be used for the production of arrays for ultimate detection of insertional mutants.

(iv) Other Methods

As previously stated, any method which may be used to enrich for a diverse collection of insertion junctions may be used with the current invention. An example of one such technique disclosed herein for the enrichment of transposon Mu-tagged sites is Amplification of Insertion Mutagenized Sites (AIMS), the procedure for which is outlined below, in Example 5 and described by Souer et al. 1995.

II. Detection of Insertional Mutants from Arrays

One aspect of the current invention which allows for efficient selection of large numbers of insertional mutants is the creation of arrays comprising insertion-junction-enriched DNA pools. The precise placement of this pooled DNA into specific arrays allows for the simultaneous screening of potentially thousands of insertion mutations. The method involves the placement and binding of DNA to known locations, termed sectors, on a solid support. Through hybridization of a desired specific probe or primer to the array, for example, insertion mutations corresponding to that gene may be identified from the total collection of insertional mutants. Further, because the amplification step may be conducted repeatedly, a large number of identical or non-identical arrays may be produced, thereby allowing simultaneous screening with many different locus-specific probes or primers.

Many different methods for preparation of arrays of DNA on solid supports are known to those of skill in the art. Specific methods of which are disclosed in, for example, Affinity Techniques, Enzyme Purification: Part B, Meth. Enz. 34 (ed. W. B. Jakoby and M. Wilchek, Acad. Press, N.Y. (1974) and Immobilized Biochemicals and Affinity Chromatography, Adv. Exp. Med. Biol. 42 (ed. R. Dunlap, Plenum Press, N. F. 1974), each specifically incorporated herein by reference in its entirety). Examples of other techniques which have been described include the use of successive application of multiple layers of biotin, avidin, and extenders (U.S. Pat. No. 4,282,287, specifically incorporated herein by reference in its entirety); through methods employing a photochemically active reagent and a coupling agent which attaches the photoreagent to the substrate (U.S. Pat. No. 4,542,102, specifically incorporated herein by reference in its entirety), use of polyacrylarnide supports on which are immobilized oligonucleotides (PCT Patent Publication No. 90/07582, specifically incorporated herein by reference in its entirety), through use of solid supports on which oligonucleotides are immobilized via a 5'-dithio linkage (PCT Patent Publication No. 91/00868, specifically incorporated herein by reference in its entirety); and through use of a photoactivateable derivative of biotin as the agent for immobilizing a biological polymer of interest onto a solid support (see U.S. Pat. No. 5,252,743; and PCT Patent Publication No. 91/07087 to Barrett et al., each specifically incorporated herein by reference in its entirety). In the case of a solid support made of nitrocellulose or the like, standard techniques for UV-crosslinking may be of particular utility (Sambrook et al., 1989).

The solid support surface upon which the array is produced may potentially be any suitable substance. Examples of materials which may be used include polymers, plastics, resins, polysaccharides, silica or silica-based materials, carbon, metals, inorganic glasses, membranes, etc. It may also be advantageous to use a surface which is optically transparent, such as flat glass or a thin layer of single-crystal silicon. Contemplated as being especially useful are nylon filters, such as Hybond N+ (Amersham Corporation, Amersham, UK). Surfaces on the solid substrate will usually, though not always, be composed of the same material as the substrate, and the surface may further contain reactive groups, which could be carboxyl, amino, hydroxyl, or the like.

It is contemplated that one may wish to use a surface which is provided with a layer of crosslinking groups (U.S. Pat. No. 5,412,087, specifically incorporated herein by reference in its entirety). Crosslinking groups could be selected from any suitable class of compounds, for example, aryl acetylenes, ethylene glycol oligomers containing 2 to 10 monomer units, diamines, diacids, amino acids, or combinations thereof. Crosslinking groups can be attached to the surface by a variety of methods that will be readily apparent to one of skill in the art. For example, crosslinking groups may be attached to the surface by siloxane bonds formed via reactions of crosslinking groups bearing trichlorosilyl or trisalkoxy groups with hydroxyl groups on the surface of the substrate. The crosslinking groups can be attached in an ordered array, i.e., as parts of the head groups in a polymerized Langmuir Blodgett film. The linking groups may be attached by a variety of methods that are readily apparent to one skilled in the art, for instance, by esterification or amidation reactions of an activated ester of the linking group with a reactive hydroxyl or amine on the free end of the crosslinking group.

The ultimate goal of producing an array in accordance with current invention, will be in screening large numbers of individuals or subsets of individuals for detection of an insertional mutant. Therefore, once the array is produced, the first step will, in a preferred embodiment, involve hybridizing the array with a solution containing a marked (labeled) probe. For detection of a mutation in a specific gene, this will typically involve the use of a cloned DNA segment including that gene sequence as a probe. Following hybridization, the surface is then washed free of unbound probe, and the signal corresponding to the probe label is identified for those regions on the surface where the probe has high affinity. Suitable labels for the probe include, but are not limited to, radiolabels, chromophores, fluorophores, chemiluminescent moieties, antigens and transition metals. In the case of a fluorescent label, detection can be accomplished with a charge-coupled device (CCD), fluorescence microscopy, or laser scanning (U.S. Pat. No. 5,445,934, specifically incorporated herein by reference in its entirety). When autoradiography is the detection method used, the marker is a radioactive label, such as $^{32}P$, and the surface is exposed to X-ray film, which is developed and read out on a scanner or, alternatively, simply scored manually. With radiolabeled probes, exposure time will typically range from one hour to several days. Fluorescence detection using a fluorophore label, such as fluorescein, attached to the ligand will usually require shorter exposure times. Alternatively, the presence of a bound probe may be detected using a variety of other techniques, such as an assay with a labeled enzyme, antibody, or the like. Other techniques using various marker systems for detecting bound ligand will also be readily apparent to those skilled in the art.

Detection may, alternatively, be carried out using PCR. In this instance, PCR detection may be carried out in situ on the slide. In this case one may wish to utilize one or more labeled nucleotides in the PCR mix to produce a detectable signal. Detection may also be carried out in a standard PCR reaction on the prepared samples to be screened. For this type of detection, the sectors in the array will not consist of DNA bound to solid support but will consist of DNA samples in solution in the wells of a microtiter dish.

It also is contemplated by the inventor that one may "reverse" the above described detection protocols. For example, instead of using amplified insertion junctions for preparation of a detectable array, one could use genetic sequences which are specific to the locus for which an insertion mutation is desired. In this case, one could label the amplified insertion junctions and use then as probes for the detection of loci corresponding to the insertion mutation. Therefore, by multiple hybridizations with different pools of amplified insertion junctions, one may ultimately identify individuals having the desired insertion mutations.

As an alternative to detection of insertion junctions with PCR or hybridizations, sequencing of insertion junctions may be used. In this procedure one would preferably first prepare pools of DNA from individuals having insertion junctions. The pools may be designed such the source of a particular insertion junction can be identified without the need for screening of all individuals within a population. An exemplary pooling procedure comprises the designation of individuals into a 2×2 grid. Pools of DNA are then prepared from all of the individuals within each column and row. The identification of a sequence in a column and a row will thereby provide a precise coordinate for the individual having that sequence. Alternatively, pools needn't be used, however, this will be less preferred as more effort will be needed to find a specific desired insertion.

III. Competitive Hybridizations

Use of the current invention may, in particular circumstances, require competitive hybridizations. This may be so when the locus-specific probe used contains one or more sequences which are repeated throughout the target genome, thereby leading to detection of multiple, non-specific loci. The situation will arise more frequently where probes are derived from genomic DNA clones of organisms which have relatively large genomes such as many mammals, and particularly plants such as maize and wheat.

Signal from repetitive sequences may be "blocked" by inclusion of unlabeled total genomic DNA in the mixture of labeled probe DNA, or by use of the unlabeled DNA in prehybridizations before application of the labeled probe. Even more effective than total genomic DNA for blocking will be DNA which is "enriched" for repetitive, such as $C_ot$-1 DNA (Zwick et al., 1997, specifically incorporated herein by reference in its entirety). It is also contemplated that one may wish to use blocking DNA which contains unlabeled sequences of the insertional mutagen. This may help to avoid detection of the insertional mutagen and help ensure only detection of the flanking sequences.

The proportion of blocking DNA to probe DNA used will vary and will depend on a number of variables. Factors upon which the concentration used is dependent include: the relative proportion of repetitive sequences in the probe/primer and target sequences, the desired level of sensitivity in the detection, the size of the repetitive sequences, and the degree of sequence homology between the probe repetitive sequences and those of the target. Typical concentrations of unlabeled blocking DNA which may be used include from about 20 to about 200 fold excess, relative to the probe, including about 30, 40, 50, 60, 70, 80, 90, 100, 110, 120, 130, 140, 150, 160, 170, 180, and 190 fold excess, Alternatively, one may wish to use concentrations of blocking DNA greater or lesser than this range, including about 10, 300, 400, 500, 600, 700, 800, 900, or about 1000 fold excess. The optimal concentration used, however, will be dependent on the above mentioned factors and will be known to those of skill in the art in light of the present disclosure. It is noted, however, that while competitive hybridizations are effective in eliminating background signal caused by repetitive sequences, it will be preferable to avoid the problem through use of unique or low copy probe sequences, such as, for example, cDNAs.

IV. Use of the Invention for Discovery of Gene Function

An important use of the current invention will be in acquiring information regarding the function of genes. Therefore, one embodiment of the invention involves the identification and isolation of a mutant for a selected gene and the use of that mutant in studies of gene function. By comparison of the phenotype of one or more individuals having a particular insertion mutation to a representative sample of individual without the mutation, inferences may be made regarding the function of the mutated sequence.

In this manner, one may begin with a cDNA or other probe or primer specific for a genetic sequence of unknown function, and, through use of the current invention, obtain information regarding the function of that sequence. In light of the high-throughput-capability of the current invention, one could, alternatively, systematically obtain large numbers of mutants and screen the mutants for identification of genes associated with traits of interest. For example, one may use a sample of plant cDNA probes to isolate maize plants having mutations corresponding the cDNAs. These mutants may then be grown in the field and various observations made of the mutant phenotype including characteristics such as yield, disease or pest resistance, stress tolerance, or any other trait deemed of interest. A correlation between a particular mutant and a phenotype will, of course, suggest that the mutated gene is involved in the expression of that trait. The mutated gene can then be cloned or used for further studies as desired by the user of the invention. Such studies may involve, for example, operably linking the cloned gene to a different promoter and using the construct created to transform plants.

V. Expression Analysis

Whereas DNA analysis techniques may be conducted using DNA isolated from any part of a plant, RNA will only be expressed in particular cells or tissue types, and hence it will be necessary to prepare RNA for analysis from these tissues. PCR techniques may also be used for detection and quantitation of RNA produced from introduced genes. In the application of PCR, it is first necessary to reverse transcribe RNA into DNA, using enzymes such as reverse transcriptase, and then, through the use of conventional PCR techniques amplify the DNA. In most instances, PCR techniques, while useful, will not demonstrate the integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques, such as ion exchange or gel exclusion chromatography. The unique structures of individual proteins offer opportunities for use of specific antibodies to detect their presence in formats such as an ELISA assay. Combinations of approaches may be employed with even greater specificity, such as western blotting, in which antibodies are used to locate individual gene products that have been separated by electrophoretic techniques. Additional techniques may be employed to absolutely confirm the identity of the product of interest, such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently, the expression of a particular mutant is determined by evaluating the phenotypic results of its expression. These assays also may take many forms, including, but not limited, to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity, which may be analyzed by near infrared reflectance spectrometry.

VI. Genetic Characterization of Insertional Mutants

To confirm the presence of one or more insertional mutants in an individual, to track these in progeny, and to analyze the effects of a particular mutation, a variety of assays may be performed. Such assays include, for example, "molecular biological" assays, such as Southern and Northern blotting and PCR; "biochemical" assays, such as detecting the presence or absence of a particular protein product, e.g., by immunological means (ELISAs and Western blots) or by enzymatic function; plant part assays, such as leaf or root assays; and also by analyzing the phenotype of the whole regenerated plant.

(i) DNA Integration, RNA Expression and Inheritance

Genomic DNA may be isolated from any plant or animal cells to determine the presence of a particular insertional event using techniques well known to those skilled in the art. The presence of an insertional mutant may, for example, be determined by polymerase chain reaction (PCR). Using this technique, discrete fragments of DNA are amplified and detected by gel electrophoresis. This type of analysis will permit one to follow a particular insertional mutant in the offspring of a cross. Insertional mutants are expected to be generated randomly and, for this reason, are expected to be unique, based on their genomic location. Thus, by designing PCR primers which will amplify segments which include both the inserting DNA and the subsequently mutated native sequence, unique amplification products which are specific to that insertion event can be identified.

Southern hybridization is especially useful for identification of particular insertional mutants, in that each insertional mutant is expected to have a unique restriction pattern. Using this technique specific, DNA sequences that were introduced into the host genome and flanking host DNA sequences can be identified. Hence, the Southern hybridization pattern of a given insertion event serves as an identifying characteristic of that transformant. The technique of Southern hybridization provides information that is obtained using PCR, e.g., the presence of an integration event, but also characterizes each individual insertion event.

Both PCR and Southern hybridization techniques can be used to demonstrate transmission of an insertional mutant to progeny. In most instances, the characteristic Southern hybridization pattern for a given insertional mutation will segregate in progeny as one or more Mendelian genes (Spencer et al., 1992), indicating stable inheritance of the transgene.

For use as a probe, one may use DNA of the insertional mutagen, from the mutated endogenous sequence, or from both. In the case of an insertional mutagen which is present in low copy, it may be desirable to use DNA from the insertional mutagen as a probe. However, where the insertional mutagen is present in high copy, such as will be the case with endogenous transposable elements, the detected restriction patterns will be complex and difficult to interpret. In this case, it may be desirable to use the endogenous, mutated sequence as a probe.

The biological sample for assays may potentially be any type of plant or animal tissue. Nucleic acid may be isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of a radiolabel or fluorescent label, or even via a system using electrical or thermal impulse signals (Affymax Technology; Bellus, 1994).

Following detection, one may compare the results seen in a given mutant with a statistically significant reference group of non-mutated controls. Typically, the non-mutated control will be of a genetic background similar to the mutated individual. In this way, it is possible to detect differences in the amount or kind of protein detected in various different mutants.

A variety of different assays are contemplated in the screening of insertional mutants isolated using the methods of the current invention. These techniques can be used to detect for both the presence of particular mutations as well as the resulting effects caused by the mutations. The techniques include, but are not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP, and PCR-SSCP.

(ii) Primers, Probes and Template-Dependent Amplifications

The term primer, as defined herein, is meant to encompass any nucleic acid that is capable of priming the synthesis of a nascent nucleic acid in a template-dependent process. Typically, primers are oligonucleotides from 10 to 20 base pairs in length, but longer sequences can be employed. Primers may be provided in double-stranded or single-stranded form, although the single-stranded form is preferred. Probes are defined differently, although they may act as primers. Probes, while perhaps capable of priming, are designed to bind to the target DNA or RNA and need not be used in an amplification process. In preferred embodiments, the probes or primers are labeled with radioactive species ($^{32}P$, $^{14}C$, $^{35}S$, $^{3}H$, or other label), with a fluorophore (rhodamine, fluorescein), an antigen (biotin, streptavidin, digoxigenin), or a chemiluminescent (luciferase).

A number of template-dependent processes are available to amplify the sequences present in a given sample. One of the best known amplification methods is the polymerase chain reaction which is described in detail in U.S. Pat. Nos. 4,683,195, 4,683,202, and 4,800,159, each specifically incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the template to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described by Sambrook et al. (1989). Alternative methods for reverse transcription utilize thermostable, RNA-dependent DNA polymerases and are described in WO 90/07641, filed Dec. 21, 1990.

Another method for amplification is the ligase chain reaction ("LCR"), disclosed in European Patent No. 0 320 308, specifically incorporated herein by reference in its entirety. In LCR, two complementary probe pairs are prepared, and, in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Patent Publication No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site, may also be useful in the amplification of nucleic acids in the present invention (Walker et al., 1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe are identified as distinctive products that are released after digestion. The original template is annealed to another cycling probe, and the reaction is repeated.

Still another amplification method, described in GB Application No. 2 202 328 and in PCT Patent Publication No. PCT/US89/01025 (each specifically incorporated herein by reference in its entirety), may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al.; PCT Patent Publication No. WO 88/10315; each specifically incorporated herein by reference in its entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double-stranded DNA molecules are heat denatured again. In either case, the single-stranded DNA is made fully double-stranded by the addition of a second target specific primer, followed by polymerization. The double-stranded DNA molecules are then multiply transcribed by an RNA polymerase, such as T7 or SP6. In an isothermal cyclic reaction, the RNA's are reverse transcribed into single-stranded DNA, which is then converted to double-stranded DNA, and then transcribed once again with an RNA polymerase, such as T7 or SP6. The resulting products, whether truncated or complete, indicate target specific sequences.

European Patent Application No. 0 329 822 (specifically incorporated herein by reference in its entirety) discloses a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle, leading to very swift amplification. With the proper choice of enzymes, this amplification can be done isothermally without the addition of enzymes at each cycle. Because of the cyclical nature of this process, the starting sequence can be chosen to be in the form of either DNA or RNA.

PCT Patent Publication No. WO 89/06700 (specifically incorporated herein by reference in its entirety) discloses a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989; each specifically incorporated herein by reference in its entirety).

Methods based on ligation of two (or more) oligonucleotides in the presence of nucleic acid having the sequence of the resulting "di-oligonucleotide," thereby amplifying the di-oligonucleotide, may also be used in the amplification step of the present invention (Wu et al., 1989, specifically incorporated herein by reference in its entirety).

(iii) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to X-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols (see Sambrook et al., 1989). For example, chromophore or radiolabeled probes or primers identify the target during or following amplification.

One example of the foregoing is described in U.S. Pat. No. 5,279,721 (specifically incorporated herein by reference in its entirety), which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optima sequencing (Pignon et al., 1994). The present invention provides methods by which any or all of these types of analysis may be used.

(iv) Design and Theoretical Considerations for Relative Quantitative RT-PCR.

Reverse transcription (RT) of RNA to cDNA followed by relative quantitative PCR (RT-PCR) can be used to determine the relative concentrations of specific mRNA species isolated from plants. By determining that the concentration of a specific mRNA species varies, it is shown that the gene encoding the specific mRNA species is differentially expressed.

In PCR, the number of molecules of the amplified target DNA increases by a factor approaching two with every cycle of the reaction until some reagent becomes limiting.

Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point, the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over-represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for plant tissue. The problem inherent in plant tissue samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5 to 100-fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that, without the internal standard/competitor, all of the reagents can be converted into a single PCR product in the linear range of the amplification curve, thus increasing the sensitivity of the assay. Another reason is that, with only one PCR product, display of the product on an electrophoretic gel or another display method becomes less complex, has less background, and is easier to interpret.

(v) Chip Technologies

Specifically contemplated by the present inventor are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al., 1989).

VII. Definitions

Corresponding Individual Lacking an Insertion Mutation: an individual which has the same genetic background as another individual, but differs on the basis of lacking a particular insertion mutation.

Detectable Array: an arrangement of nucleic acid sequences from which specific sequences or subsets of sequences can be identified. The array can comprise DNA sequences bound to a solid support and can also include DNA compositions arranged in solution in suitable containers. For the purposes of the current invention the sequences will be ones which may be used to identify one or more specific insertion junctions. These sequences can, therefore, represent DNA of insertion junctions or, alternatively, sequences representing a particular locus for which an insertion mutation is desired.

DNA Composition Enhanced for a Plurality of Insertion Junctions: a DNA composition in which a non-locus specific selection of insertion junctions has been enhanced relative to the starting DNA from which the DNA composition is derived. Such non-locus specific selections are prepared without the need for use of probes or primers which are specific to the locus or loci for which an insertion mutation is desired. The selection procedure will typically, instead, use probes or primers which are specific to the insertional mutagen. Examples of such procedures include inverse PCR, primer adapted PCR, and vectorette PCR, AIMS, or any other amplification or isolation procedure which is capable of being used to enhance a DNA composition for a diverse class of insertion junctions.

Hybridization Filter: an object to which nucleic acids can be fixedly attached, and to which probes may be hybridized, for example, in Southern Hybridization. Exemplary hybridization filters will be made of nitrocellulose or nylon, although any similar materials may also be used.

Insertion Junction: the segment of DNA encompassing the end of an insertional mutagen and particularly, the flanking genomic DNA into the insertional mutagen has inserted. For the purposes of the invention, DNA from the insertional mutagen itself need not typically be present, but for detection, the flanking genomic DNA should be.

Insertional Mutagen: any sequence which is capable of inserting into a segment of genomic DNA thereby causing an insertion mutation.

Microscope Slide: an object similar to a standard slide used for holding a specimen to be observed under a microscope. The microscope slide will preferably be made of glass or a similar material and will have a flat surface, however, it will be understood to those of skill in the art that various trivial modifications may be made to a typical microscope slide and still not depart from the scope and meaning of the term as defined in the current invention.

Pool: a composition of DNA made from the combination of DNA from multiple individuals. The pool will typically be constructed to allow the identification of individuals possessing a desired genetic sequence from a populations of individuals without necessitating screening of every individual within that population.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Considerations in the Preparation of Arabidopsis Insertional Mutation Populations A project was initiated to saturate the Arabidopsis genome with insertion mutations. Based on the Arabidopsis genome size (100 Mb) and an average gene target size (2 kb), it was calculated that 100,000 random insertions would make hitting any unique gene segment (2 kb) a probable event (p>90%), assuming integration sites are chosen randomly.

Individual Arabidopsis plants were vacuum infiltrated according to Bechtold et al. 1993, allowed to set seed, and seed was plated to determine the frequency and pattern of transformation events. Independent insertions were selected with application of FINALE® (glufosinate herbicide). The transformation frequency, based on the total number of seed, was between 1 and 2%. Examination of several hundred individual siliques indicated that, based upon T-DNA hybridization patterns, most, if not all, transformed plants were derived from independent T-DNA transformation events.

The $T_1$ transgenic plants contained between 1 and 20 T-DNA hybridizing bands. Some of these bands represent junction fragments between tandem (direct and inverted) repeats of T-DNA, while others represented unique junction fragments between plant DNA and T-DNA. Several plants were outcrossed to wild-type plants, and the $T_2$ outcross progeny were examined by Southern analysis to determine the number of independent loci based on recombination between T-DNA bands. By examining large numbers of progeny crosses, it was ascertained that most $T_1$ plants contained between 1 and 5 independent T-DNA loci.

It was thus shown that: 1) transgenic Arabidopsis can be directly selected in soil using phosphinothricin resistance; 2) the frequency of transformation averaged 1.5% of the total seed; 3) that most, if not all, $T_1$ resistant plants represented independent transformation events; and 4) that $T_1$ plants contained an average of 3 independent T-DNA insertion loci per genome Therefore, to generate 100,000 independent insertions, about 35,000 phosphinothricin-resistant (i.e., transformed) $T_1$ plants are needed. At an average transformation frequency of 1.5% and a total seed population of about 5,000 seeds per plant, it was decided to vacuum infiltrate about 2,000 $T_0$ plants to achieve saturation.

Example 2

Generation of Arabidopsis Insertional Mutants and DNA Pools

Five to six *Arabidopsis thaliana* seeds were germinated in pots and grown at 21° C. under 16 hr light. Primary bolts were removed, and when secondary bolts emerged, the plants were vacuum infiltrated with an Agrobacterium strain harboring the T-DNA containing the bar gene driven by the constitutive viral promoter CaMV35S (Bechtold et al., 1993; White et al. 1990; SEQ ID NO:1). A total of over 2,000 plants were vacuum infiltrated and allowed to self-pollinate. Seeds were collected from individual pots, vernalized, and germinated in soil at a density of approximately 10,000 seeds per pot. After seedlings emerged, they were sprayed with FINALE® herbicide (BASF Inc.) 1 time per week, for up to 6 weeks, using the manufacturers recommended level of application. Non-transformed plants died, while transgenic plants thrived under selection.

When the primary bolts emerged from the 100–150 resistant $T_1$ plants in each pot, tissue was harvested for DNA extraction to generate the $T_1$ DNA pool. For DNA extraction, four to sixteen leaf punches were placed in each tube of a 96 cluster tube rack (CoStar Inc., Cat#4410). Samples were cooled in a liquid nitrogen bath, or alternatively, lyophilized overnight and ground to a powder with a wooden stick or glass rod on dry ice. Following grinding, 5 zirconium beads were added (2.5 mm, Zirconia Silica Beads, Biospec Products, Inc.) to each tube and the samples capped (Microplate Sealers Titer Tops from Diversified Biotech, Catalog #TTOPS). The sample plate was placed onto a bead beater (Biospec Products, Inc.) and shaken for 1 min on medium setting. Then 0.5 ml of prewarmed (65° C.) extraction buffer (100 mM Tris pH8, 50 mM EDTA, 1% SDS, 500 mM NaCl) was added, the samples capped, vortexed, and allowed to incubate at 65° C. for 10 min in a water bath. One hundred sixty milliliters cold 5 M Kac was added, and samples were capped, mixed by inverting, and placed on ice for 5 min. The tube rack was then spun at 3000 rpm for 10 min in a table top plate carrier.

The supernatant (300 ml) was then transferred to a filtaplate (course, 96 well 300 μl FiltaPlate Plus; Polyfiltronics FP350PSC/CF/D) and 300 ml 4.4M $NH_4OAc$/Isopropanol (1:7 ratio) was added with a 20 ml Quick-Precip Plus (AGTC 72641) to an 800 ml receiver plate (96 well 800 μl Receiver plates, AGTC 22304). The filter plate was stacked on the receiver plate and the crude extract spun into a capture plate at 3000 rpm for 5 min. The capture plate was capped and mixed by an inverting spin at 3000 rpm 10 min. The plate was inverted to empty isopropanol, 200 μl 70% EtOH was added to pellet the DNA, and the plate was inverted to empty the EtOH, followed by air drying of the pellet. Once the pellet was dry, 100 ml of TE (TE (10/1) pH 8+0.4 mg/ml Rnase) is added, the samples covered and vortex on slow. The DNA is stored at 4° C.

The $T_1$ plants were then allowed to mature and set seed to generate corresponding $T_2$ seed pools. A total of 384 pools of 100–150 $T_1$ plants were produced along with $T_1$ DNA and $T_2$ seed pools. Each pool represented an average of 125 plants containing, on average, 4 independent insertions per genome, or a estimated total of over 203,650 T-DNA insertions.

The population of Arabidopsis thaliana plants having insertion mutations was organized in Collections, Sets, and Pools of $T_1$ DNA and $T_2$ seed. Collections (a, b, c, . . . ) were defined by the T-DNA construct (i.e., Collection "a" contains the 35S::bar gene and a synthetic supF gene for junction fragment rescue; SEQ ID NO:1). Each Collection consisted of three or more Sets (1, 2, 3, . . . ) of 96 Pools (designated alphanumerically A01-H12) per Set. Hence, Collection "a" consists of 384 pools labeled a1.A01 through a3.H12. Each pool, represents approximately 300–500 independent T-DNA insertions. Hence, a Collection contains a total of 288 Pools (285 transgenic pools plus 3 control pools) and represents approximately 85,000 to 140,000 independent T-DNA insertions.

Example 3

Confirmation of the Generated Population of Arabidopsis Insertional Mutants

To confirm that the generated population contained the predicted number of insertional mutants, standard site-selected mutagenesis was applied to locate insertions in several genes of interest, including the two cytosine DNA methyltransferase genes (MET1 and MET2). First, Set a1 (pools a1.A01 through a1.H12) was screened using a PCR reaction containing a gene-specific primer designed to the 3' UTR together with a right border T-DNA primer designed just inside the right border junction.

The Set a1 $T_1$ DNA pools were screened with one of the four gene-specific primers together with the right border primer. Five microliters of the PCR reactions was denatured and applied to a membrane in a 96-well manifold, and membranes were hybridized with the appropriate gene-specific probes. In each case, from 1 to 3 insertion alleles could be detected for all four genes from Set a1 pools, a result consistent with the estimate of T-DNA insertion copy number. If the left border primer detects a similar number of insertions in opposite orientation with respect to transcription, it is estimated that the YATDL collection would contain between 8 and 24 alleles for each Arabidopsis gene. This assumes all genes are targets for T-DNA insertion. If the four chosen targets were typical ones, any two Sets (i.e., a1 and a2) should contain at least two alleles in most Arabidopsis genes.

Example 4

Enriching for Mu-Tagged Sites by Amplification of Insertion Mutagenized Sites (AIMS)

Maize plants having Mu insertion mutations are organized into 32×32 grids. DNA is then extracted from individual maize plants using the procedure of Example 19, and pools of the DNA are made for each row and column. The pooled DNA is digested either with the restriction endonuclease Bfal or the enzyme Msel. For restriction of 500 ng DNA, 5 U of Msel or Bfal is placed in a 40 μl volume of 1× RL-Buffer for 1 h at 37° C. (1× RL contains 10 mM Tris-Acetate, pH 7.5, 10 mM Mg-Acetate, 50 mM K-Acetate, and 50 ng/μl BSA). Linker sequences (Msel/Bfal) are ligated by adding together 1 μl 50 μM Msel or Bfal adapter, 1 μl 10× Ligation Buffer (Boehringer), 1 U T4-DNA Ligase, and water to a final volume of 50 μl, followed by incubation for at least 2 h at 37° C. (European Patent application 92402629, specifically incorporated herein by reference in its entirety). For amplification of the Mu-element insertion sequences, a linear PCR is performed using a biotinylated primer complementary to the Mu-element ends (Mu-Bio), and the amplification product is separated with streptavidin-coated magnetic beads. The PCR mix for the linear amplification is composed of approximately 27.5 μl DNA, 2.5 μl 12 μM Mu-Biotin primer, 10 μl 2.5 mM dNTPs (each), 5 μl 10× KCl V buffer, and 1 U Taq DNA polymerase (Boehringer) in a final volume of 50 μl. Amplification is carried out in 12 cycles using the following PCR program:

1: 94° C.            3 min
2: 94° C.            1 min
3: 65° C.            30 sec
4: 72° C.            60 sec
cycle 4 to 2, 11 times (Use of more than 12 cycles can cause aberrant exponential PCR amplification)
6: 72° C.            3 min.
Primer and adapter sequences ('-3' orientation) are as follows:
Mser/Bfal Adapter:   TACTCAGGACTCAT
                     GACGATGAGTCCTGAG
Mu-Bio:              AGAGAAGCCAACGCCA(A/T)CGCCTCCATT
Msel Sel/A(GCT):     GATGAGTCCTGAGTAA/A(GCT)
Bfal Sel/A(GCT):     GATGAGTCCTGAGTAG/A(GCT)
Mu Sel:              TCTATAATGGCAATTATCTC For removal of excess Mu-Biotin primer, a QIA-quickspin column is used as follows: add 250 μl PB buffer to 50 μl PCR reaction; spin; wash column with 2 600 μl PE; elute with 50 μl TE, pH 8.5; add 50 μl 4 M NaCl to 50 μl eluat; spin down briefly; use directly for PCR. The isolated biotin-labeled sequences are amplified by PCR with Bfal or Msel linker-specific primer (Msel Sel/A or Bfal Sel/A). The radioactive labeled nested Mu-specific primer (Mu Sel) is prepared in 20 reactions, each containing 2.5 μl of 10 μM Mu Sel, 5 μl Gamma ATP (50 μCi), 1.25 μl One Phor All+buffer (Pharmacia), and 1–2.5 U T4 Polynucleotide Kinase, in a total volume of 12.5 μl. To lower the complexity of the amplified sequences, the linker-specific primer has a one nucleotide extension at its 3'-end, and individual reactions are made for all eight linker primers. Exponential PCR is carried out with the labeled primer in a reaction containing 5 µl beads/DNA (suspend well before pipetting), 0.5 µl labeled Mu Sel Primer, 0.6 µl 10 µM MseI Sel/N or BfaI Sel/N, 4.0 µl 2.5 mM dNTPs, 2.0 µl 10× Ammonium sulphate buffer, and 2.0 µl BSA 1 mg/ml in a final volume of 17 µl, covered with paraffin. The PCR program is as follows:

| 1) | 94° C. | pause |
|---|---|---|
|  |  | add 1 U Taq polymerase in 3 µl volume and continue |
| 2) | 94° C. | 1 min |
| 3) | 65° C. | 30 sec |
|  |  | decrease by 0.7° C. every cycle |
| 4) | 72° C. | 1 min |
|  |  | cycle 4 to 2 18× |
| 5) | 94° C. | 1 min |
| 6) | 52° C. | 30 sec |
| 7) | 72° C. | 1 min |
|  |  | cycle 7 to 5 26× |
| 8) | 72° C. | 3 min |

Following amplification of the Mu insertion junctions, the DNA may be used for preparation of arrays and subsequent detection of insertional mutants. Alternatively, Mu-tagged sites may be amplified using vectorette PCR, IPCR, or other techniques.

Example 5

Amplification of Insertion Junctions Using Primer-adapted PCR

Sau3AI-digested genomic DNA (50 µg) is separated on a 1% agarose gel, and size fractions of approximately 500 and 900 bp are excised from the gel and purified using a GeneClean® kit (Bio 101, La Jolla, Calif.). Ligation of adapters is performed in a total volume of 20 µl of adapter-ligation buffer (66 mM Tris-HCl, pH 7.6; 10 mM MgCl$_2$; 10 mM dithiothreitol [DTT]; 0.3 mM ATP; 1 mM spermidine-HCl; and 200 µg/ml bovine serum albumin [BSA]) with 200 ng adapters, 2–5 µg genomic DNA, and 1 U T4-DNA ligase (GIBCO BRL/Life Technologies, Gaithersburg, Md.). The ligation reaction is incubated at 16° C. overnight, and the non-ligated adapters are removed by spin-column purification (Sephacryl® S-300, Pharmacia LKB Biotechnology AB, Uppsala, Sweden). The columns are equilibrated with PCR buffer (50 mM KCl; 10 mM Tris-HCl, pH 8.3; and 1.5 mM MgCl$_2$) and eluted in 50 µl volume.

An insertional mutagen complementary primer is first used for a linear amplification of the insertion junction sequences. The reaction mixture of 100 µl contains 200 µM deoxynucleoside triphosphates (dNTP), 1× PCR buffer (Promega, Madison, Wis.), 20 pmol biotinylated primer 1, 30 µl of adapter-ligated genomic DNA template, and 1 U Taq DNA polymerase (Promega). The temperature program is a two-step program of 50 cycles comprising 95.5° C. for 30s and 70° C. for 2 min 30 s on the PCR machine PHC-2 (Techne, Cambridge, UK). The linear biotinylated products are bound to Dynabeads® M-280 Streptavidin (Dynal A.S., Oslo, Norway); 0.25 mg beads are washed prior to binding (twice with 1 M NaCl in TE buffer (10 mM Tris-HCl, pH 8.0, and 1 mM EDTA) and once with 1× PCR buffer) and then incubated for 5 min at room temperature (RT) with the amplified product. After binding, the supernatant containing the genomic DNA is removed by fixing the beads with the magnet MPC-E (Dynal) and discarding the supernatant. The beads are washed 3 times with 1 M NaCl in TE buffer, 3 times with TE buffer, and once with PCR buffer.

Exponential PCR is then performed on the single-stranded template bound to the beads, with the 100 µl of reaction mixture containing 200 µM dNTP, 1× PCR buffer, 50 pmol of each of the adapter-primer and the non-biotinylated primer 1, and 1 U Taq DNA polymerase. The temperature program is 35 cycles of 95.5° C. for 30 s, 62° C. for 1 min, and 72° C. for 1 min. A second exponential PCR of 35 cycles is performed under the same conditions as above using 1 µl of the obtained PCR product in 100 µl reaction mixture and replacing primer 1 with the nested primer 2.

The PCR products may then be directly used for the preparation of arrays or can be "blunted" using Klenow polymerase (David et al., 1986) and subcloned into the SmaI site of pBluescript® (Stratagene, La Jolla, Calif.). The inserts can then be completely sequenced on both strands or can be used to transform bacteria for the production of additional insertion DNA.

Example 6

Amplification of Insertion Junctions Using Vectorette PCR

Prepared DNAs are digested with appropriate restriction enzymes in suitable buffers at 37° C. for 1 h ATP, dithiothreitol (DTT) is added to a concentration of 2 mM, and appropriate vectorette (commercially available from Clonetech Inc., Palo Alto, Calif.) units are added along with 1 U T4-DNA ligase (without a change of buffer). The samples are then incubated at 20° C. for 1 h followed by 37° C. for 30 min. This incubation cycle is carried out a further two times because the vectorettes are designed so that the restriction enzyme site is not reformed on ligation of the vectorette to target DNA; this incubation cycle leads to increased target-vectorette constructs. The incubation at 37° C. leads to digestion of target-target DNA but not target-vectorette constructs. PCR is performed using the appropriate known biotinylated primer and vectorette PCR primer in µl× Taq PCR buffer with 2.5 U Taq DNA polymerase (Promega). PCRs may be carried out, for example, using a Techne PHG 1 unit, with 40 cycles of 96° C. for 1 min, 64° C. for 1 min, and 74° C. for 1.5 min. PCR products are visualized on a 1% agarose gel stained with ethidium bromide and/or used directly for array preparation.

Example 7

Amplification of Insertion Junctions Using Inverse-PCR

Restriction digests are carried out using 5 µg of source DNA treated with 10 U EcoRI according to the supplier's specifications (U.S. Biochemicals). Digested DNAs are electrophoresed thorough a 1.1% (w/v) agarose gel (SeaKem) in 1× TBE buffer (50 mM Tris; 100 mM Borate; and 10 mM EDTA, pH 8.2). Appropriate fragments are excised from the gel, electroeluted in 0.5× TBE, and extracted twice with phenol and once with chloroform; and the DNA concentration is determined by UV spectrophotometry.

For circularization, 0.1 µg of the appropriate restriction fragment is diluted to a concentration of 0.5 µg/ml in ligation buffer (50 mM Tris HCl, pH 7.4; 10 mM MgCl$_2$; 10 mM dithiothreitol; 1 mM adenosine triphosphate; and 10 µg/ml gelatin). This ligation reaction is initiated by the addition of T4-DNA ligase (New England Biolabs) to a concentration of 1 U/µl, and the reaction is allowed to proceed for 16 h at 12° C. The ligated sample is then treated with an equal volume of phenol:chloroform mixture, the aqueous phase is removed, and the DNA is precipitated with ethanol and collected by centrifugation.

The PCR is performed manually in reactions containing 0.1 μg of circularized DNA obtained as described above in the presence of 50 pmol of each primer and 500 μM dNTPs. The primers are synthesized using an Applied Biosystems automated oligonucleotide synthesizer. Thirty cycles of denaturation are carried out at 94° C. for 1.5 min, followed by primer annealing at 48° C. for 1.0 min and extension by Taq DNA polymerase (Perkin-Elmer Cetus) at 70° C. for 4.0 min. The resulting sample is desalted, and excess dNPTs are removed with a Centricon 30 microconcentration column from Amicon (Higuchi et al., 1988; Saiki et al., 1988). The DNA products from the PCR reactions are then used for the production of arrays for detection of specific insertional mutants or cloned into appropriate vectors.

Example 8

Screening $T_1$ DNA Pools by PCR

PCR screening may be used as an alternative to hybridization of gridded arrays of PCR-amplified T-DNA::plant junction fragments representing insertions in all 384 $T_1$ DNA pools. Initially, two $T_1$ DNA Sets are screened per gene (192 reactions) in a 192-well plate. This format is preferred to a 384 format because each gene screen can be barcoded and handled separately. This format can be easily managed with two robotics units, a Hydra 96 unit (Robbins Scientific, Sunnyvale Calif.) to efficiently dispense $T_1$ DNA templates and a Beckman Biomek 2000 automatic liquid handling unit fitted with a chilled base to assemble PCR reactions. This strategy should, on average, identify between 2 to 6 insertions per gene. Using two four-block PCR instruments (MJ Research PTC225), PCR screens may be performed on 8 genes per cycle, or a minimum of 40 genes per week.

Approximately 5 μl of the reaction is then denatured and applied to a filter membrane via a manifold apparatus. Gene-specific primers are used to simultaneously amplify and radiolabel an appropriate region of the provided cDNA clone using a PCR instrument dedicated for radioactive reactions. Primers are removed by spun columns, and the probe is denatured and hybridized to the filter membranes overnight according to Example 11. The following day, the filters are washed and imaged using a phosphoimager.

Example 9

Multiplexing $T_2$ Seed Pools

This is dependent upon whether or not a pool has previously been multiplexed. If it has, the $T_2$ screen starts directly with the PCR step detailed below. For non-multiplexed pools, providing $T_3$ seed harboring an insertion allele requires one additional Arabidopsis generation (8 weeks from start to finish). The frequency of this delay decreases in proportion to the number of pools multiplexed, however. It will be preferable to multiplex all pools and utilize direct $T_2$ screening to locate the $T_3$ seed pool.

The number of $T_2$ plants needed to screen to have a 95% probability of recovering any particular insertion can be estimated. Assuming that the homozygous condition is non-lethal, 480 $T_2$ plants are needed; should the homozygous condition result in lethality, this number increases to 864 plants.

Based on the calculations, the technique to multiplex $T_2$ pools is as follows: approximately 1000 $T_2$ seeds are vernalized and suspended in 0.1% agarose. The seed-containing solution is pipetted onto the surface of 96 pots to yield approximately 8–10 seeds per pot. After germination, seedlings are thinned back to 5 plants per pot, for a total of 480 plants. This number gives a 95.8% chance of recovering a non-lethal allele and an 80.4% probability for recovering recessive lethals. Initially, this strategy is more preferred than screening two sets of 480 (960) plants from a single $T_1$ pool because more time and resources are used generating independent $T_2$ DNA and $T_3$ seed pools. This means that more pools are available sooner and insertions may be more rapidly identified. Since 4–8 hits are expected per gene in a primary screen, a high probability of recovering missed lethals can be achieved by simply screening a different $T_2$ pool of 480 plants, rather than multiple sets from one $T_2$ pool.

At the time of bolting, tissue (one leaf per plant, 5 leaves per $T_2$ pool) is placed into a deep 96-well plate and lyophilized. All $T_2$ DNA samples are extracted simultaneously in a deep 96-well plate using the technique in Example 2, to yield enough high quality DNA for over 500 PCR reactions. After seed set, the $T_3$ seed is collected from individual pots and stored in alphanumeric coordinates of a deep 96-well plate.

To identify the $T_3$ seed pool containing the insertion of interest, the $T_2$ DNA is pooled by row (8 individuals) and column (12 individuals), and a PCR screen (8+12=20 reactions per pool, 2 pools per gene for a total of 40 PCR reactions per gene) and a dot blot hybridization are performed (alternatively, this step may be accomplished by gridding and hybridization to PCR-amplified junction fragments in a 96-array format). The row and column coordinate of the $T_3$ seed pool containing the insertion allele of interest is determined by the hybridization pattern. Initially, two multiplex pools are chosen per gene to provide two independent alleles; more are done if needed (i.e., the insertion is not found in the 480-plant multiplex pool).

Example 10

High Density Filter Construction

Fifty to 100 ng of DNA from the pools of amplified insertion junctions are placed in 96-well microtiter plates and dotted using the "Saturnin" robot of Généthon onto nylon filters of 8×12 cm (Hybond N+, Amersham Corporation, Amersham, UK) at an array density of 16 microtiter plates arrayed in a 4×4 format. DNA is cross-linked to the membrane by ultraviolet radiation (120 mJ/cm$^2$) using the Stratagene UV-Stratalinker 2400 (Stratagene, LaJolla, Calif.). Control clones are also spotted at specific positions on the filter. Membranes are prepared in batches and stored at 4° C. before use. The procedure is repeated until the desired number of sectors have been prepared.

Example 11

Probe Preparation, Labeling, and Hybridization

The locus specific probe, comprising a single or low copy sequence is labeled with 50 μCi of [γ-$^{33}$]ATP·(Amersham) (3000 Ci/mmole) using 10 U T4 polynucleotide kinase (Boehringer Mannheim, Mannheim, Germany) for 30 min at 37° C. Filters are incubated within glass tubes in an hybridization oven (Appligène, Strasbourg, France) in a volume of 15 ml. Membranes in duplicate are prehybridized for 5 hr at 42° C. in a 15-ml solution containing final concentrations of 4× SSC (1× SSC=150 mM NaCl and 15 mM sodium citrate), 50% formamide, 10× Denhart's, 0.1% sodium dodecyl sulfate (SDS), 8% dextran sulfate, 50 mM phosphate buffer (pH 7.2), and 1 mM EDTA. Hybridization of the replicate set of filters is performed overnight at 42° C. in the same solution with 15 to 20×10$^6$ cpm of $^{33}$P-radiolabeled probes in the presence of 100 µg/ml of denatured herring sperm DNA. In the case of probes which contain one or more repetitive sequences which may cause non-gene specific hybridization, some or all of the herring sperm DNA is replaced with either total genomic DNA or $C_o$t-1 DNA. This DNA will hybridize competitively with the repeated elements and effectively block their signal. The membranes are washed twice for 10 min in 2× SSC/0.1% SDS, followed by washing once for 15 min 1× SSC/0.1% SDS and twice for 15 min in 0.1× SSC 0.1% SDS. All washes are carried out at 65° C. Exposure to phosphor screens is for 1 to 3 days.

Stripping of hybridized membranes is performed by two successive immersions in a solution of 0.4 M NaOH and 0.1% SDS at 65° C. for 30 min. Membranes are rinsed in 0.2 M Tris-HCl (pH 8.0) and 1× SSC/0.1% SDS for 10 min at room temperature. Membranes may be used a minimum of 5 of times.

Hybridization of the membranes with the $^{33}$P-radiolabeled oligonucleotide probe is performed in 7% SDS, 0.5 M phosphate buffer (pH 7.2), and 1 mM EDTA for 15 hr at 50° C., followed by washing in 2× SSC for 15 min at 50° C., followed by 15 min at room temperature and a final wash in 1× SSC/0.1% SDS for 15 min at 37° C.

Example 12

Hybridization Signal Analysis

Filters are scanned on the PhosphorImager imaging Plate system (Molecular Dynamics, Sunnyvale, Calif.) for quantitative analysis of signal intensities. After image acquisition, the scanned 16-bit images are imported on a Sun workstation and image analysis is performed using the XdotsReader software (Cose, Le Bourget, France).

The software processes the results of an exposure into images of individual filters and then translates the hybridization signal coordinates into dot localization on the filter using a reference grid for the arrangement of the dots. It takes into account slight variations in dot position attributable to filter deformation by assigning the signal detected to the nearest position expected. The software quantifies each dot individually after local background subtraction. These tasks, image cutting, dot identification, and dot quantification are processed sequentially and automatically. The results are validated interactively, and a table is generated that contains for each dot its reference number and the experimental values.

Different types of values may be obtained for the quantification of the dot intensity: the radius of the dot, the mean of the dot pixel intensities for one dot, the maximal intensity of the pixels of the dot, the sum of the pixel intensities of the dot, and the average of the pixel intensities of the dot weighted by the distance to the center of the dot. To take into account experimental variations in specific activity of the probe preparations or exposure time that might alter the signal intensity, the data obtained from different hybridizations may be normalized by dividing the Im for each dot by the average of the intensities of all the dots present of the filter to get a normalized Im value (nIm).

Example 13

Rehybridization of Nucleic Acids to Oligonucleotide-Derivatized Substrate Surface The arrays are hybridized with labeled probe in accordance with the procedure of Example 14, and then washed three times with a 100° C. solution of 0.01% SDS. The slides are then allowed to expose XAR film overnight at –70° C. to confirm the labeled probe is removed. Rehybridization with the labeled probe is carried out using the Stratagene Qwik-Hyb(tm) hybridization accelerator solution following the package insert directions. Other hybridization acceleration reagents that can be employed in the methods of the present invention include A1 protein, RecA protein, SSB, dextran sulfate, ficoll, phenol, and detergent.

Prehybridization is carried out for 15 minutes at 53.5° C., and then 100 µl of 10 mg/ml salmon sperm DNA is added to the slides together with 10 µl of the labeled probe. The hybridization reaction is carried out at 53.5° C. for one hour. The slides are washed and then allowed to expose XAR film overnight at –70° C.

Example 14

Identifying Individual Arabidopsis Plants with Insertion Alleles

Once an appropriate $T_3$ seed pool has been identified, the last step is to find the individual plant(s) harboring the insertion. Southern analysis of approximately 25 $T_3$ plants (p=97% chance of identifying a homozygote or heterozygote in the $T_3$) is a preferred method for this purpose.

Some types of mutations may not be found or may be difficult to find. For instance, dominant lethality or sterility mutations will be lost in the $T_1$ generation and not present in the collection. Recessive lethality or sterility is less problematic. There may be instances in which a mutation is identified in the $T_2$ multiplex screen, but absent in the $T_3$ seed—e.g. male or female sporophytic sterility will be undetected at the time of tissue sampling. This problem may be avoided, however, because of the high number of expected hits (from 4–8). Since the phosphoimager data will be saved electronically, should no $T_3$ plant be found harboring the mutation of interest, additional $T_3$ seed may simply be screened, or additional $T_2$ DNA PCR screens may be used to identify additional $T_3$ pools.

Example 15

Introgression of an Insertion Mutation Into Elite Inbreds and Hybrids

It is specifically contemplated by the inventor that an insertional mutation identified by the current invention may provide a plant with a desired characteristic and that one may therefore wish to move the insertion mutation from one genetic background into another. Backcrossing may be used to achieve this goal. Backcrossing can be used to transfer a specific trait from one source to an inbred that lacks that trait. This can be accomplished, for example, by first crossing a superior inbred (A) (recurrent parent) to a donor inbred (non-recurrent parent), which carries the appropriate mutation. The progeny of this cross are first selected in the resultant progeny for the mutation to be transferred from the non-recurrent parent, and then the selected progeny are mated back to the superior recurrent parent (A). After five or more backcross generations with selection for the desired trait, the progeny are hemizygous for the mutant loci, but are like the superior parent for most or almost all other genes. The last backcross generation would be selfed to give progeny which are pure breeding for the insertional mutagen(s) being transferred, i.e., one or more integration events.

Example 16

Marker-Assisted Selection

Genetic markers may be used to assist in the introgression of one or more integration events from one genetic background into another. Marker-assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired integration event which otherwise has a non-agronomically desirable genetic background is crossed to an elite parent, genetic markers may be used to select progeny which not only possess the integration event of interest but also have a relatively large proportion of the desired germplasm. In this way, the number of generations required to introgress one or more insertion events into a particular genetic background is minimized.

In the process of marker-assisted breeding, DNA sequences are used to follow particular traits in the process of plant breeding (Tanksley et al., 1989). In terms of the present invention, such a desirable trait may comprise, for example, a particular insertion event of a transgene or an endogenous element such as a transposon. Marker-assisted breeding may be undertaken as follows. Seeds of plants with the desired trait are planted in soil in the greenhouse or in the field. Leaf tissue is harvested from the plants for preparation of DNA at any point in growth at which approximately one gram of leaf tissue can be removed from each plant without compromising the viability of the plant. Genomic DNA is isolated using a procedure modified from Shure et al. (1983). Approximately one gram of leaf tissue from each seedling is lypholyzed overnight in 15 ml polypropylene tubes. Freeze-dried tissue is ground to a powder in the tubes using a glass rod. Powdered tissue is mixed thoroughly with 3 ml extraction buffer (7.0 urea, 0.35 M NaCl; 0.05 M Tris-HCD, pH 8.0; 0.01 M EDTA; and 1% sarcosine). Tissue/buffer homogenate is extracted with 3 ml phenol/chloroform. The aqueous phase is separated by centrifugation and precipitated twice using 1/10 volume of 4.4 M ammonium acetate (pH 5.2) and an equal volume of isopropanol. The precipitate is washed with 75% ethanol and resuspended in 100–500 $\mu$l TE (0.01 M Tris-HCl and 0.001 M EDTA, pH 8.0).

Genomic DNA is then digested with a 3-fold excess of restriction enzymes, electrophoresed through 0.8% agarose (FMC), and transferred (Southern, 1975) to Nytran (Schleicher and Schuell) using 10× SCP (20× SCP=2 M NaCl, 0.6 M disodium phosphate and 0.02 M disodium EDTA). The filters are prehybridized in 6× SCP, 10% dextran sulfate, 2% sarcosine, 500 $\mu$g/ml denatured salmon sperm DNA, and $^{32}$P-labeled probe generated by random priming (Feinberg & Vogelstein, 1983). Hybridized filters are washed in 2× SCP and 1% SDS at 65° C. for 30 minutes and visualized by autoradiography using Kodak XAR5 film. Genetic polymorphisms which are genetically linked to traits of interest are thereby used to predict the presence or absence of the traits of interest.

Those of skill in the art will recognize that there are many different ways to isolate DNA from plant tissues and that there are many different protocols for Southern hybridization that will produce identical results. Those of skill in the art will recognize that a Southern blot can be stripped of radioactive probe following autoradiography and re-probed with a different probe. In this manner, one may identify each of the various integration events that are present in the plant. Further, one of skill in the art will recognize that any type of genetic marker which is polymorphic at the region(s) of interest may be used for the purpose of identifying the relative presence or absence of a trait and that such information may be used for marker assisted breeding.

Each lane of a Southern blot represents DNA isolated from one plant. Through the use of multiplicity of gene integration events as probes on the same genomic DNA blot, the integration event composition of each plant may be determined. Correlations may be established between the contributions of particular integration events to the phenotype of the plant. Only those plants that contain a desired combination of integration events may be desired for advancement to maturity and use for pollination. DNA probes corresponding to particular integration events are useful markers during the course of plant breeding to identify and combine particular integration events without having to grow the plants and assay the plants for agronomic performance.

It is expected that one or more restriction enzymes will be used to digest genomic DNA, either singly or in combinations. One of skill in the art will recognize that many different restriction enzymes will be useful, and the choice of restriction enzyme will depend on the DNA sequence of the transgene integration event that is used as a probe and the DNA sequences in the genome surrounding the transgene. For a probe, one will want to use DNA or RNA sequences which will hybridize to the DNA used for transformation. One will select a restriction enzyme that produces a DNA fragment following hybridization that is identifiable as the transgene integration event. Thus, particularly useful restriction enzymes will be those which reveal polymorphisms that are genetically linked to specific transgenes or traits of interest.

Example 17

Utilization of Insertionally Mutated Crops

One embodiment of the current invention has, as an ultimate goal, the production of novel plants which will be useful to man. Such plants may comprise a transformation event having a selected site of integration, may comprise in their genomes a desired insertion mutation, or may be transformed with one or more genes the function of which has been determined with the current invention. It is specifically contemplated by the inventor that such plants may be used for virtually any purpose deemed of value. For example, one may wish to harvest seed from plants with a particular insertion event or transgene. This seed may in turn be used for a wide variety of purposes. The seed may be sold to farmers for planting in the field or may be directly used as food, either for animals or humans. Alternatively, products may be made from the seed itself. Examples of products which may be made from the seed include, oil, starch, animal or human food, pharmaceuticals, and various industrial products. Such products may be made from particular plant parts or from the entire plant. One product made from the entire plant which is deemed of particular value is silage for animal feed.

Means for preparing products from plants, such as those that may be identified with the current invention, have been well known since the dawn of agriculture and will be known to those of skill in the art in light of the instant disclosure. Specific methods for crop utilization may be found in, for example, Sprague et al. (1988), and Watson et al. (1987).

Example 18

General Methods for Assays

DNA analysis is performed as follows. Genomic DNA is isolated using a procedure modified from Shure et aL (1983). Approximately 1 gm tissue is ground to a fine powder in liquid nitrogen using a mortar and pestle. Powdered tissue is mixed thoroughly with 4 ml extraction buffer (7.0 M urea; 0.35 M NaCl; 0.05 M Tris-HCl, pH 8.0; 0.01 M EDTA; and 1% sarcosine). Tissue/buffer homogenate is extracted with 4 ml phenol/chloroform. The aqueous phase is separated by centrifugation, passed through Miracloth, and precipitated twice using 1/10 volume of 4.4 M ammonium acetate (pH 5.2) and an equal volume of isopropanol. The precipitate is washed with 70% ethanol and resuspended in 200–500:1 TE (0.01 M Tris-Hcl and 0.001 M EDTA, pH 8.0).

The presence of a particular sequence in a plant may be detected through the use of polymerase chain reaction (PCR). Using this technique, specific fragments of DNA can be amplified and detected following agarose gel electrophoresis. For example, two hundred to 1000 ng genomic DNA is added to a reaction mix containing 10 mM Tris-HCl (pH 8.3); 1.5 mM $MgCl_2$; 50 mM KCl; 0.1 mg/ml gelatin; 200 $\mu$M each dATP, dCTP, dGTP, and dTTP; 0.5 $\mu$M each forward and reverse DNA primers; 20% glycerol; and 2.5 U Taq DNA polymerase. The reaction is run in a thermal cycling machine as follows with 39 repeats of the cycle: 94° C. for 3 min, 94° C. for 1 min, 50° C. for 1 min, an for 30 s, followed by 72° C. for 5 min. Twenty $\mu$l of each reaction mix is run on a 3.5% NuSieve gel in TBE buffer (90 mM Tris-borate and 2 mM EDTA) at 50 V for two to four hours. Using this procedure, for example, one may detect the presence of a bar gene integration event using the forward primer CATCGAGACAAGCACGGTCAACTTC and the reverse primer AAGTCCCTGGAGGCACAGGGCT-TCAAGA.

For Southern blot analysis, genomic DNA is digested with a 3-fold excess of restriction enzymes, electrophoresed through 0.8% agarose (FMC), and transferred (Southern, 1975) to Nytran (Schleicher and Schuell) using 10× SCP (20× SCP=2 M NaCl, 0.6 M disodium phosphate, and 0.02 M disodium EDTA). Filters are prehybridized at 65° C. in 6× SCP, 10% dextran sulfate, 2% sarcosine, and 500 $\mu$g/ml heparin (Chomet et al., 1987) for 15 min. Filters then are hybridized overnight at 65° C. in 6× SCP containing 100 $\mu$g/ml denatured salmon sperm DNA and $^{32}$P-labeled probe. Filters are washed in 2× SCP and 1% SDS at 65° C. for 30 min and visualized by autoradiography using Kodak XAR5 film. For rehybridization, the filters are boiled for 10 min in distilled $H_2O$ to remove the first probe and then prehybridized as described above.

Example 19

Selection of Desirable Transformation Events

It is specifically contemplated by the inventor that the current invention may be used to select for transformation events which are located in a particular region of a genome. This is significant, because the genomic location of a transformation event will greatly influence the expression of a transgene. Therefore, one may determine regions of the genome in which a transgene will be highly expressed, clone DNA from that region, and then use that clone to select transformation events from the region of interest using that probe.

All of the methods disclosed and claimed herein can be made and executed without undue experimentation in light of the present disclosure. While the methods of this invention have been described in terms of the preferred embodiments, it will be apparent to those of skill in the art that variations may be applied to the methods and in the steps or in the sequence of steps of the methods described herein without departing from the concept, spirit, and scope of the invention. More specifically, it will be apparent that certain agents which are both chemically and physiologically related may be substituted for the agents described herein while achieving the same or similar results. All such similar substitutes and modifications apparent to those skilled in the art are deemed to be within the concept, spirit, and scope of the invention as defined by the appended claims.

REFERENCES

The following references, to the extent that they provide exemplary procedural or other details supplementary to those set forth herein, are specifically incorporated herein by reference in their entirety.

European Patent Application No. 92402629
European Patent No. 0 273 085
European Patent No. 0 320 308
European Patent No. 0 329 822
European Patent No. 0 439 330
PCT Patent Publication No. US 87/00880
PCT Patent Publication No. WO 88/10315
PCT Patent Publication No. US 89/01025
PCT Patent Publication No. WO 89/06700
PCT Patent Publication No. WO 90/07582
PCT Patent Publication No. WO 90/07641
PCT Patent Publication No. WO 91/00868
PCT Patent Publication No. WO 91/07087
PCT Patent Publication No. WO 94/09699
United Kingdom Patent No. 2 202 328
U.S. Pat. No. 4,282,287
U.S. Pat. No. 4,542,102
U.S. Pat. No. 4,683,195
U.S. Pat. No. 4,683,202
U.S. Pat. No. 4,732,856
U.S. Pat. No. 4,800,159
U.S. Pat. No. 4,883,750
U.S. Pat. No. 4,994,370
U.S. Pat. No. 5,252,743
U.S. Pat. No. 5,279,721
U.S. Pat. No. 5,384,253
U.S. Pat. No. 5,384,256
U.S. Pat. No. 5,412,087
U.S. Pat. No. 5,445,934
U.S. Pat. No. 5,508,184
U.S. Pat. No. 5,523,222
U.S. Pat. No. 5,538,880
U.S. Pat. No. 5,550,318
U.S. Pat. No. 5,591,616
U.S. Pat. No. 5,629,183
U.S. Pat. No. 5,279,721
U.S. Pat. No. 5,279,721
U.S. Pat. No. 5,279,721
Arumuganathan et al., "Nuclear DNA content of some important plant species," *Plant Mol. Biol. Rep.*, 9:208–218 (1991).
Azpiroz-Leehan et al. "T-DNA insertion mutagenesis in Arabidopsis going back and forth. Trends Genet 13 (1997)
Ballinger et al., *Proc. Natl. Acad. Sci. USA*, 86:9402–9406 (1989).
Ballinger, D. G., et al., "Targeted gene mutations in Drosophila," *Proc. Natl Acad. Sci. USA*, 86:9402–9406 (1989).
Bechtold et al., "Transformation of Arabidopsis by vacuum infiltration", *C. R. Acad. Sci.* Paris 316,1194–1199, (1993)
Bechtold, N., Bouchez, D., "In planta Agrobacterium-mediated transformation of adult *Arabidopsis thaliana* plants by vacuum infiltration" In: Gene transfer to plants. Potrykus, I. and G. Spangenberg (Eds.).Springer-Verlag: Berlin, Germany; New York, N.Y., pp19–23 (1995)

Bellus, *J. Macromol. Sci. Pure Appl. Chem*, A31(1):1355–1376 (1994).

Bennetzen, "Transposable element Mu1 is found in multiple copies only in Robertson's Mutator maize lines," *J. Mol. Appl. Genet.*, 2:519–524 (1984).

Bennet et al., "Nuclear DNA amounts in angiosperms," *Phil. Trans. R. Soc. Lond. B.*, 274:227–274 (1976).

Callis et al., *Genes and Develop.*, 1:1183–1200, (1987).

Cannon et al., *Plant Mol. Biol.*, 15:39–47 (1990).

Chen et al., "High-efficiency transformation of mammalian cells by plasmid DNA," *Mol. Cell. Biol.*, 7:2745–2752 (1987).

Chomet et al., *EMBO J*, 6:295–302, 1987.

Christou et al., *Plant Physiol*, 87:671–674, 1988.

Church, G., et al., "Multiplex DNA sequencing," *Science*, 240:185–188 (1988).

Collins et al., "Directional cloning of DNA fragments at a large distance from an initial probe: a circularization method," *Proc. Natl. Acad. Sci. USA*, 81:6812–6816 (1984).

Cotten et al., "High efficiency receptor-mediated delivery of small and large (48 kilobase) gene constructs using the endosome disruption activity of defective or inactivated adenovirus particles," *Proc. Natl. Acad. Sci. USA*, 89:6094–6098 (1992).

Curiel, "Gene transfer mediated by adenovirus-polylysine DNA complexes," In: *Viruses in Human Gene Therapy*, J.-M. H. Vos (Ed.), Carolina Academic Press, Durham, N.C., pp. 179–212 (1994).

Davis et al. In: *Basic Methods in Molecular Biology*, Elsevier Science Publishing, New York, N.Y. (1986).

DeBlock et al. "Two T-DNAs co-transformed into *Brassica napus* by a double *Agrobacterium tumefaciens* infection are mainly integrated at the same locus" Theor. Appl Genet. 82 (1991)

Depicker, A. (1985)"Frequencies of simultaneous transformation with different T-DNAs and their relevance to the Agrobacterium cell interaction. Mol. Gen. Genet. 201, 477–484.

Epselund et al., "A simple method for generating single-stranded DNA probes labeled to high activities," *Nucleic Acids Res.*, 18:6157–6158 (1990).

Espelund et al., "Late embryogenesis-abundant genes encoding proteins with different numbers of hydrophilic repeats are regulated differentially by abscisic acid and osmotic stress," *Plant J.*, 2:241–252 (1992).

Faloona et al., "Specific synthesis of DNA in vitro via a polymerase chain reaction," *Methods Enzymol.*, 155:335–350 (1987).

Fechheimer et al., "Transfection of mammalian cells with plasmid DNA by scrape loading and sonication loading," *Proc. Natl. Acad. Sci. USA*, 84:8463–8467 (1987).

Feinberg et al., *Anal Biochem*, 132:6–13 (1983).

Fodor et al., "Light-directed, spatially addressable parallel chemical synthesis," *Science*, 251:767–773 (1991).

Fors et al., "Cloning of the shark Po promoter using a genomic walking technique based on the polymerase chain reaction," *Nucleic Acids Res.*, 18:2793–2799 (1990).

Forsthoefel et al., "T-DNA insertion mutagenesis in Arabidopsis: prospects and perspectives," *Aust. J. Plant Physiol.*, 19:353–366 (1992).

Fraley et al., *Proc. Natl. Acad. Sci. USA*, 80:4803, (1983).

Fraley et al., "Entrapment of a bacterial plasmid in phospholipid vesicles:potential for gene transfer," *Proc. Nat'l. Acad. Sci. USA*, 76:3348–3352 (1979).

Freifelder et al., *Physical Biochemistry Applications to Biochemistry and Molecular Biology*, 2nd ed., Wm. Freeman and Co., New York, N.Y. (1982).

Frohman, PCR Protocols: *A Guide to Methods and Applications*, Academic Press, New York, N.Y. (1990).

Fromm et al., *Nature*, 312:791–793, (1986).

Galau et al., "Abscisic acid induction of cloned cotton late embryogenesis-abundant (Lea) mRNAs," *Plant Mol. Biol.*, 7:155–170 (1986).

Geiser et al., "Genomic clones of a wild-type allele and a transposable elements-induced mutant allele," *The EMBO Journal*, 1:1455–1460 (1982).Ghosh and Bachhawat, "Targeting of liposomes to hepatocytes," In: Wu G. and C. Wu ed. *Liver Diseases, Targeted Diagnosis and Therapy Using Specific Receptors and Ligands*. New York: Marcel Dekker, pp. 87–104 (1991).

Gopal, "Gene transfer method for transient gene expression, stable transformation, and cotransformation of suspension cell cultures," *Mol. Cell. Biol.*, 5:1188–1190 (1985).

Graham et al., "A new technique for the assay of infectivity of human adenovirus 5 DNA," *Virology*, 52:456–467 (1973).

Hacia et al., "Detection of heterozygous mutations in BRCA1 using high density oligonucleotide arrays and two-colour fluorescence analysis," *Nature Genetics*, 14:441–447 (1996).

Harland et al., "Translation of mRNA injected into Xenopus oocytes is specifically inhibited by antisense RNA," *J. Cell Biol.*, 101: 1094–1099 (1985).

Higuchi et al., "DNA typing from single hairs," *Nature*, 332:543–545 (1988).

Hultman et al., "Bidirectional solid-phase sequencing of in vitro-amplified plasmid DNA," *BioTechniques*, 10:84–93 (1991).

Hultman et al., "Direct solid phase sequencing of genomic and plasmid DNA using magnetic beads as solid support," *Nucleic Acids Res.*, 17:4937–4946 (1989).

Kaeppler et al. (1990) Plant Cell Reports 9: 415–418.

Kaiser, K., et al., "'Site-selected' transposon mutagenesis of Drosophila," *Proc. Natl. Acad. Sci. USA*, 87:1686–1690 (1990).

Kaneda et al., "Increased expression of DNA cointroduced with nuclear protein in adult rat liver," *Science*, 243:375–378 (1989).

Kato et al., "Expression of hepatitis β virus surface antigen in adult rat liver," *J. Biol. Chem.*, 266:3361–3364 (1991).

Kelleher et al., "Long-term episomal gene delivery in human lymphoid cells using human and avian adenoviral-assisted transfection," *Biotechniques*, 17(6):1110–1117 (1994).

Klein et al., "High-velocity microprojectiles for delivering nucleic acids into living cells," *Nature*, 327:70–73 (1987).

Klein et al., "Transfer of Foreign Genes into Intact Maize Cells using High Velocity Microprojectiles," *Proc. Natl. Acad. Sci. USA*, 85:4305–4309, (1988).

Koes, R. et al "Targeted gene inactivation in petunia by PCR-based selection of transposon insertion mutants. Proc. Natl. Acad. Sci. USA 92 8149–8153 (1995)

Kooter et al., *Curr. Opin. Biotechnol.*, 4:166–171 (1993).

Krysan et al., "Identification of transferred DNA insertions within Arabidopsis genes involved in signal transduction and ion transport. Proc. Nati. Acad. Sci. USA 93, 8145–8150. (1996)

Kwoh et al., *Proc. Natl. Acad. Sci. USA*, 86:1173 (1989).

Lorz et al., *Mol Gen Genet*, 199:178–182, (1985)

Maniatis et al., In: *Molecular Cloning: A Laboratory Manual*, Cold Spring Harbor Laboratory Press, Cold Spring Harbor, N.Y. (1982).

McKinney et al. "Sequence-based identification of T-DNA insertion mutations in Arabidopsis actin mutants act2-1 and act4-1. Plant J. 8,613–622. (1995)

Meinke, "Perspectives on genetic analysis of plant embryogenesis," *Plant Cell*, 3:857–866 (1991).

Mueller et al., "In vivo footprinting of a muscle specific enhancer by ligation mediated PCR," *Science*, 246:78–786 (1989).

Murray et al., "Rapid isolation of high molecular weight plant DNA," *Nucl. Acids Res.*, 8:4321–4325 (1980).

Napoli et al., *Plant Cell*, 2:279–289 (1990).

Newman, T., et al., "Genes galore: A summary of methods for assessing results from large-scale partial sequencing of anonymous Arabidopsis cDNA clones," *Plant Phys.*, 106:1241–1255 (1994).

Nicolau et al., "Liposome-mediated DNA transfer in eukaryotic cells: dependence of the transfer efficiency upon the type of liposomes used and the host cell cycle stage," *Biochim. Biophys. Acta*, 721:185–190 (1982).

Nicolau et al., "Liposomes as carriers for in vivo gene transfer and expression," *Methods Enzymol.*, 149:157–176 (1987).

Ochman and Selander, "Standard reference strains of *Escherichia coli* from natural populations," *J. Bacteriol.*, 157:690–693 (1984).

Ochman et al., "Genetic applications of an inverse polymer chain reaction," *Genetics*, 120:621–625 (1988).

Ohara et al., *Proc. Natl. Acad. Sci. USA*, 86:5673–5677 (1989).

Omirulleh et al., *Plant Molecular Biology*, 21:415–428, (1993).

Pease et al., "Light-generated oligonucleotide arrays for rapid DNA sequence analysis," *Proc. Natl. Acad. Sci. USA*, 91:5022–5026 (1994).

Perales et al., *Proc. Natl. Acad. Sci. USA*, 91:4086–4090 (1994).

Pignon et al., *Hum. Mutat.*, 3:126–132 (1994).

Potrykus et al., *Mol Gen Genet*, 199:183–188, 1985.

Potter et al., "Enhancer-dependent expression of human k immunoglobulin genes introduced into mouse pre-B lymphocytes by electroporation," *Proc. Natl Acad. Sci. USA*, 81:7161–7165 (1984).

Rippe et al., "DNA-mediated gene transfer into adult rat hepatocytes in primary culture," *Mol. Cell Biol.*, 10:689–695 (1990).

Rosenthal and Jones, "Genomic walking and sequencing by oligocassette mediated polymerase chain reaction," *Nucleic Acids Res.*, 18:3095–3096 (1990).

Rosenthal et al., "PCR walking from microdissection close M54 identifies three exons from the human gene for the neural cell adhesion molecule L1 (CAM-L1)," *Nucleic Acids Res.*, 19:5395–5401 (1991).

Rushforth, A. M., et al., "Site-selected insertion of the transposon Tc1 into a Caenorhabditis elegans myosin light chain gene," *Mol. Cell. Biol.*, 13:029–910 (1993).

Saiki et al., "Primer directed enzymatic amplification of DNA with a thermostable DNA polymerase," *Science*, 239:487–491 (1988).

Saiki et al., "Enzymatic amplification of β-globin genomic sequences and restriction site analysis for diagnosis of sickle cell anemia," *Science*, 230:1350–1354 (1985).

Sambrook et al., *Molecular Cloning, A Laboratory Manual*, 2nd ed., (1989).

Sawyer et al., "Distribution and abundance of insertion sequences among natural isolates of *Escherichia coli*," *Genetics*, 115:51–63 (1987).

Scharf et al., "Direct cloning and sequence analysis of enzymatically amplified genomic sequences," *Science*, 233:1076–1078 (1986).

Schmidt et al., "Transposon tagging and molecular analysis of the maize regulatory locus opaque-2," *Science*, 238:960–963 (1987).

Schwarz-Sommer et al., *Science*, 250:931–936 (1990).

Shapiro, *Handbook of Biochemistry and Molecular Biology*, CRC Press, Cleveland, Ohio., pp. 313–318 (1976).

Shoemaker et al., "Quantitative phenotypic analysis of yeast deletion mutants using a highly parallel molecular barcoding strategy," *Nature Genetics*, 14:450–456 (1996).

Shure et al., *Cell*, 35:225–233 (1983).

Silver et al., *J Cell Biochem.* (Suppl.), 13E:306 (1989).

Souer et al., *Plant Journal* 7, 677–685 (1995),.

Southern, *J Mol Biol*, 98:503–517 (1975).

Spencer et al. *Proceeding of the NATO Advanced Study Institute on Plant Molecular Biology*, 81(H):559–565 (1993).

Talbert et al., "Mu transposable elements are structurally diverse and distributed throughout the genus Zea," *J. Mol. Evol.*, 29:28–39 (1989).

Tanksley et al., *Bio/Technology*, 7:257–264 (1989).

Tinland, B. "The integration of T-DNA into plant genomes" Trends in Plant Sci. 1,178–184 (1996)

Triglia et al., "A procedure for in vitro amplification of DNA segments that lie outside the boundaries of known sequences," *Nucleic Acids Res.*, 16:8186 (1988).

Tur-Kaspa et al., "Use of electroporation to introduce biologically active foreign genes into primary rat hepatocytes," *Mol. Cell Biol.*, 6:716–718 (1986).

Van der Krol et al., *Nature* (London), 333:866–869 (1988).

Van der Krol et al., *Plant Cell*, 2:291–299 (1990a).

Van der Krol et al., *Mol. Gen. Genet.*, 220:204–212 (1990b).

Vasil et al., "Herbicide-resistant fertile transgenic wheat plants obtained by microprojectile bombardment of regenerable embryogenic callus," *Biotechnology*, 10:667–674, 1992.

Vasil et al., *Plant Physiol.*, 91:1575–1579, 1989.

Wagner et al., *Science*, 260:1510–1513 (1990).

Walker et al., *Proc. Natl. Acad. Sci. USA*, 84:6624–6628 (1987).

Walker et al., *Proc. Natl. Acad. Sci. USA*, 89:392–396 (1992).

White, J. et al. "A cassette containing the bar gene of *Streptomyces hygroscopicus*: a selectable marker for plant transformation. Nucleic Acids Research. 18. (1990)

Wong et al., "Appearance of β-lactamase activity in animal cells upon liposome mediated gene transfer," *Gene*, 10:87–94 (1980).

Wu and Wu, "Receptor-mediated in vitro gene transfections by a soluble DNA carrier system," *J. Biol. Chem.*, 262:4429–4432 (1987).

Wu and Wu, *Adv. Drug Delivery Rev.*, 12:159–167 (1993).

Wu et al., *Genomics*, 4:560 (1989).

Xiang, C. and Guerra, D. J. *Plant Physiol.*, 102:287–293 (1993).

Yang et al., "In vivo and in vitro gene transfer to mammalian somatic cells by particle bombardment," *Proc. Nat'l Acad. Sci. USA*, 87:9568–9572 (1990).

Yanofsky, M. F., et al., "The protein encoded by the Arabidopsis homeotic gene agamous resembles transcription factors," *Nature*, 346:35–39 (1990).

Zwaal, R. R., et al., "Target-selected gene inactivation in *Caenorhabditis elegans* by using a frozen transposon insertion mutant bank," *Proc. Natl Acad. Sci. USA*, 90:7431–7435 (1993).

Zwick, M. S., et al. "A rapid procedure for the isolation of $C_o$t-1 DNA from plants" Genome 40(1) 138–142 (1997).

What is claimed is:

1. A method of identifying an insertion event in a genome comprising the steps of:
   (a) preparing a DNA composition enhanced for a plurality of insertion junctions;
   (b) preparing at least a first detectable array comprising said DNA composition, wherein said preparing comprises directly or indirectly attaching said DNA composition to a solid support; and
   (c) detecting said insertion event from said first array.

2. The method of claim 1, wherein said DNA composition is a first DNA composition and further comprising preparing a second DNA composition enhanced for a plurality of insertion junctions, wherein said second DNA composition differs from said first DNA composition in the makeup of said insertion junctions.

3. The method of claim 2, wherein said step of preparing said first DNA composition comprises amplification of insertion junctions with inverse PCR.

4. The method of claim 2, wherein said step of preparing said first DNA composition comprises amplification of insertion junctions with vectorette PCR.

5. The method of claim 2, wherein said step of preparing said first DNA composition comprises amplification of insertion junctions with primer-adapted PCR.

6. The method of claim 2, wherein said step of preparing said first DNA composition comprises amplification of insertion junctions with AIMS.

7. The method of claim 2, wherein the detectable array comprises said first and second DNA compositions arranged on a solid support.

8. The method of claim 7, wherein the solid support is a microscope slide.

9. The method of claim 8, wherein said insertion event is detected by hybridization with a fluorescently labeled DNA probe.

10. The method of claim 9, wherein said insertion event is detected by hybridization with a probe labeled with an antigen, and said antigen is detected with a molecule which binds said antigen.

11. The method of claim 8, wherein said insertion event is detected by PCR.

12. The method of claim 7, wherein said solid support comprises a hybridization filter.

13. The method of claim 12, wherein said insertion event is detected by hybridization with a radioactively-labeled DNA probe.

14. The method of claim 13, wherein said step of detecting comprises hybridization of a gene-specific probe to said array.

15. The method of claim 2, wherein said array comprises a plurality of DNA pools, said pools comprising DNA from at least said first and second DNA compositions.

16. The method of claim 1, wherein said DNA composition comprises plant DNA.

17. The method of claim 16, wherein said plant DNA is further defined as monocot plant DNA.

18. The method of claim 17, wherein said monocot plant DNA is still further defined as derived from a species selected from the group consisting of maize, rice, wheat, barley, sorghum, oat, and sugarcane.

19. The method of claim 18, wherein said monocot DNA is maize DNA.

20. The method of claim 16, wherein said plant DNA is further defined as dicot plant DNA.

21. The method of claim 20, wherein said dicot DNA is further defined as derived from a species selected from the group consisting of cotton, tobacco, tomato, soybean, sunflower, oil seed rape (canola), alfalfa, potato, strawberry, onion, broccoli, Arabidopsis, pepper, and citrus.

22. The method of claim 21, wherein said DNA composition is still further defined as comprising *Arabidopsis thaliana* DNA.

23. The method of claim 1, wherein said DNA composition comprises animal DNA.

* * * * *